US006133505A

United States Patent [19]
Gronenborn

[11] Patent Number: 6,133,505
[45] Date of Patent: Oct. 17, 2000

[54] PHYTOPATHOGENIC GEMINIVIRUS RESISTANT TRANSGENIC PLANTS AND SEEDS AND METHODS FOR OBTAINING SAME BY INTRODUCTION OF MUTATED C1 GENE

[75] Inventor: Bruno Gronenborn, Gif-sur-Yvette, France

[73] Assignee: Centre National de la Recherche Scientifique, Paris Cedex, France

[21] Appl. No.: 08/809,103

[22] PCT Filed: Sep. 15, 1995

[86] PCT No.: PCT/FR95/01192

§ 371 Date: Mar. 17, 1997

§ 102(e) Date: Mar. 17, 1997

[87] PCT Pub. No.: WO96/08573

PCT Pub. Date: Mar. 21, 1996

[30] Foreign Application Priority Data

Sep. 15, 1994 [FR] France .................................. 94 11040

[51] Int. Cl.⁷ .................................................... C12N 15/82
[52] U.S. Cl. ........................................... 800/280; 435/440
[58] Field of Search ................................. 435/172.3, 419, 435/320.1, 440, 69.1, 468; 800/205, 250, 280, 279, 301

[56] References Cited

U.S. PATENT DOCUMENTS 5,850,023 12/1998 Elmer et al. ............................ 800/205

FOREIGN PATENT DOCUMENTS

WO 95/03404 2/1995 WIPO .

OTHER PUBLICATIONS

Von Arnim et al. Inhibition of African cassava mosaic virus systemic infection by a movement protein from the related geminivirus tomato golden mosaic virus. Virology. 187:555–564, Apr. 1992.

Longstaff et al. Extreme resistance to potato virus X infection in plants expressing a modified component of the putative viral replicase. The EMBO Journal. 12(2):379–386, 1993.

Jupin et al. DNA replication specificity of TYLCV geminivirus is mediated by the amino–terminal 116 amino acids of the Rep protein. FEBS Letters. 362:116–120, 1995.

A. Von Arnim et al., "Inhibition of African Cassava Mosaic Virus Systemic Infection by a Movement Protein from the Related Geminivirus Tomato Golden Mosaic Virus", *Virology*, vol. 187, pp. 555–564, 1992.

A.G. Day et al., "Expression of an antisense viral gene in transgenic tobacco confers resistance to the DNA virus tomato golden mosaic virus", *Proceedings of the National Academy of Sciences of USA*, vol. 88, 1991 Washington, pp. 6721–6725.

J. Stanley et al., "Defective viral DNA ameliorates symptoms of geminivirus infection in transgenic plants", *Proceedings of the National Academy of Sciences of USA*, vol. 87, 1990 Washington, pp. 6291–6295.

T. Kunik et al., "Transgenic Tomato Plants Expressing the Tomato Yellow Leaf Curl Virus Capsid Proteins are Resistant to the Virus", *Biotechnology*, vol. 12, No. 5, May 1994, New York, pp. 500–504.

T.M.A. Wilson, "Strategies to protect crop plants against viruses: Pathogen–derived resistance blossoms", *Proceedings of the National Academy of Sciences of USA*, vol. 90, Apr. 1993 Washington, pp. 3134–3141.

F De Kouchkovsky et al., "Molecular Biology of Tomato Yellow Leaf Curl Virus (TYLCV) and Potential Ways to Control the Disease", *Molecular Biology of Tomato Yellow Leaf Curl Virus*, 1993, pp. 227–238.

S.F. Hanson et al., "Site–Specific Mutations in Codons of the Putative NTP–Binding Motif on the AL1 Gene of Bean Golden Mosaid Deminivirus Abolish Infectivity", *Annual Meeting of the American Phytopathological Society*, St. Louis, Missouri, Aug. 17–21, 1991, p. 1247.

*Primary Examiner*—Amy J. Nelson
*Attorney, Agent, or Firm*—Young & Thompson

[57] ABSTRACT

Nucleotide sequences produced by mutation (also known as mutant nucleotide sequences) of C1 nucleotide sequences present in a pathogenic geminivirus genome in plants with one or more mutations capable of producing a dominant negative phenotype for the replication of the pathogenic virus, its diffusion in a plant, or its spread from one plant to another, especially through vectors such as insects, the mutant nucleotide sequences being capable of fully or partially inhibiting the replication and/or diffusion and/or spread of the pathogenic virus for producing phytopathogenic geminivirus resistant or tolerant transgenic plants.

4 Claims, 14 Drawing Sheets

Figure 1

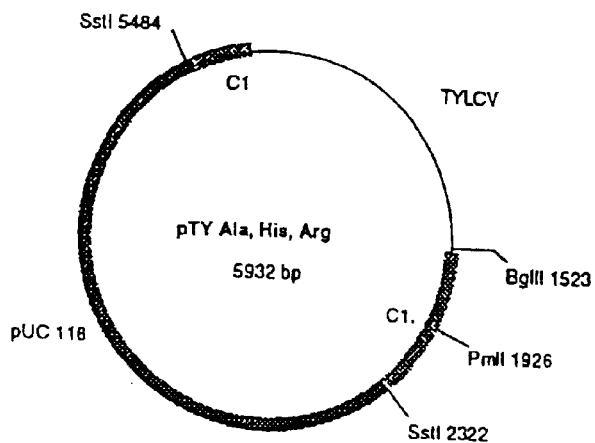
Figure 2 A
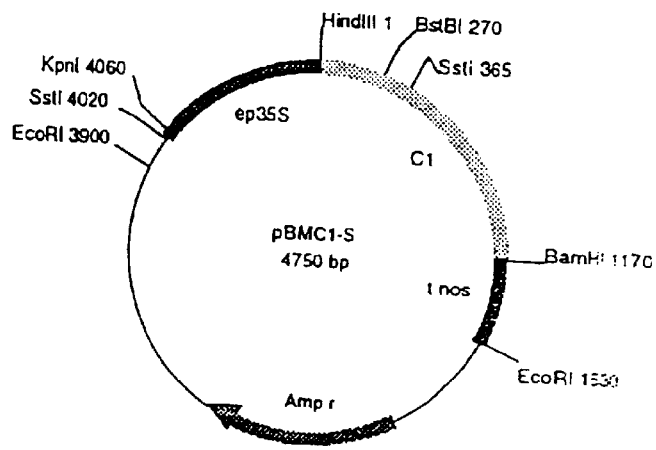
Figure 2 B
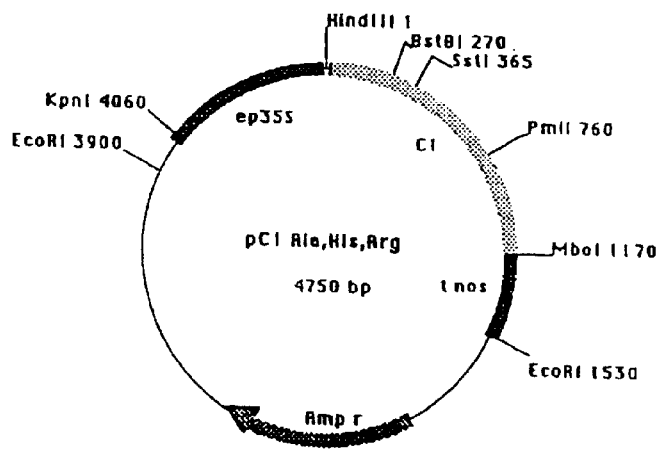
Figure 2 C
Figure 2

G   X   X   X   X   G   K   S/T

GLY  ASP  SER  ARG  THR  GLY  LYS  THR
GGT  GAC  AGC  CGG  ACA  GGA  AAG  ACA

GCG............A L A

CAT............H I S

AGG............A R G

Figure 3

```
C1*      ATGCCAAGATCAGGTCGTTTTAGTATCAAGGCTAAAAATTATTTCCTTACATATCCCAAA
                                                                    60
RepK227A  M   P   R   S   G   R   F   S   I   K   A   K   N   Y   F   L   T   Y   P   K
                                                                    20

C1*      TGTGATTTAACAAAAGAAAATGCACTTTCCCAAATAACAAACCTACAAACACCCACAAAC
                                                                    120
RepK227A  C   D   L   T   K   E   N   A   L   S   Q   I   T   N   L   Q   T   P   T   N
                                                                    40

C1*      AAATTATTCATCAAAATTTGCAGAGAACTACATGAAAATGGGGAACCTCATCTCCATATT
                                                                    180
RepK227A  K   L   F   I   K   I   C   R   E   L   H   E   N   G   E   P   H   L   H   I
                                                                    60

C1*      CTCATCCAATTCGAAGGAAAATACAATTGTACCAATCAACGATTCTTCGACCTGGTATCC
                                                                    240
RepK227A  L   I   Q   F   E   G   K   Y   N   C   T   N   Q   R   F   F   D   L   V   S
                                                                    80

C1*      CCAACCAGGTCAGCACATTTCCATCCGAACATTCAGGGAGCTAAATCGAGCTCCGACGTC
                                                                    300
RepK227A  P   T   R   S   A   H   F   H   P   N   I   Q   G   A   K   S   S   S   D   V
                                                                    100

C1*      AAGTCCTATATCGACAAGGACGGAGATGTTCTTGAATGGGGTACTTTCCAGATCGACGGA
                                                                    360
RepK227A  K   S   Y   I   D   K   D   G   D   V   L   E   W   G   T   F   Q   I   D   G
                                                                    120

C1*      CGATCTGCTAGGGGAGGACAACAGACAGCCAACGACGCTTACGCAAAGGCAATTAACGCA
                                                                    420
RepK227A  R   S   A   R   G   G   Q   Q   T   A   N   D   A   Y   A   K   A   I   N   A
                                                                    140

C1*      GGAAGTAAGTCGCAGGCTCTTGATGTAATTAAAGAATTAGCGCCTAGAGATTACGTTCTA
                                                                    480
RepK227A  G   S   K   S   Q   A   L   D   V   I   K   E   L   A   P   R   D   Y   V   L
                                                                    160

C1*      CATTTTCATAATATAAATAGTAATTTAGATAAGGTTTTCCAGGTGCCTCCGGCACCTTAT
                                                                    540
RepK227A  H   F   H   N   I   N   S   N   L   D   K   V   F   Q   V   P   P   A   P   Y
                                                                    180

C1*      GTTTCTCCTTTTTTATCTTCTTCTTTCGATCAAGTTCCTGATGAACTTGAACACTGGGTT
                                                                    600
RepK227A  V   S   P   F   L   S   S   S   F   D   Q   V   P   D   E   L   E   H   W   V
                                                                    200

C1*      TCCGAGAACGTCATGGATGCCGCTGCGCGGCCTTGGAGACCGGTGAGTATAGTGATTGAG
                                                                    660
RepK227A  S   E   N   V   M   D   A   A   A   R   P   W   R   P   V   S   I   V   I   E
                                                                    220
```

Figure 13

```
                            AgG (PmlI)
                            cAt
C1*         GGTGACAGCCGGACAGGAgcGACcACGTGGGCCCGTTCATTAGGCCCACATAATTATTTG
                                                                        720
RepK227A    G   D   S   R   T   G   A   T   T   W   A   R   S   L   G   P   H   N   Y   L
RepK227H                            H                                                   240
RepK227R                            R
                                    227

C1*         TGCGGCCATCTTGACCTCAGTCAAAAAGTATACAGCAATAATGCTTGGTATAACGTCATT
                                                                        780
RepK227A    C   G   H   L   D   L   S   Q   K   V   Y   S   N   N   A   W   Y   N   V   I
                                                                                        260

C1*         GATGACGTCGACCCGCATTATTTAAAACACTTTAAAGAATTTATGGGGGCCCAAAGAGAT
                                                                        840
RepK227A    D   D   V   D   P   H   Y   L   K   H   F   K   E   F   M   G   A   Q   R   D
                                                                                        280

C1*         TGGCAAAGCAACACAAAGTATGGCAAGCCCATTCAAATTAAAGGAGGCATTCCCACTATC
                                                                        900
RepK227A    W   Q   S   N   T   K   Y   G   K   P   I   Q   I   K   G   G   I   P   T   I
                                                                                        300

C1*         TTCCTATGCAATCCAGGCCCACAATCATCATTTAAAGAATATCTCGACGAAGAAAAAAAT
                                                                        960
RepK227A    F   L   C   N   P   G   P   Q   S   S   F   K   E   Y   L   D   E   E   K   N
                                                                                        320

C1*         CAAGCATTAAAAAACTGGGCTACTAAGAATGCAATCTTCGTCACCATCCACCAGCCATTG
                                                                        1020
RepK227A    Q   A   L   K   N   W   A   T   K   N   A   I   F   V   T   I   H   Q   P   L
                                                                                        340

C1*         TTCGCAGATACCAATCAAAATACAACATCACATCGCCAAGAAGAGGCAAGTGAGGCGTAG
                                                                        1081
RepK227A    F   A   D   T   N   Q   N   T   T   S   H   R   Q   E   E   A   S   E   A
                                                                                    359
```

Figure 13 (suite 1)

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 1148 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: 1..1077

(xi) SEQUENCE DESCRIPTION: SEQ ID NO:1:

```
ATG CCA AGA TCA GGT CGT TTT AGT ATC AAG GCT AAA AAT TAT TTC CTT      48
Met Pro Arg Ser Gly Arg Phe Ser Ile Lys Ala Lys Asn Tyr Phe Leu
 1               5                  10                  15

ACA TAT CCC AAA TGT GAT TTA ACA AAA GAA AAT GCA CTT TCC CAA ATA      96
Thr Tyr Pro Lys Cys Asp Leu Thr Lys Glu Asn Ala Leu Ser Gln Ile
             20                  25                  30

ACA AAC CTA CAA ACA CCC ACA AAC AAA TTA TTC ATC AAA ATT TGC AGA     144
Thr Asn Leu Gln Thr Pro Thr Asn Lys Leu Phe Ile Lys Ile Cys Arg
         35                  40                  45

GAA CTA CAT GAA AAT GGG GAA CCT CAT CTC CAT ATT CTC ATC CAA TTC     192
Glu Leu His Glu Asn Gly Glu Pro His Leu His Ile Leu Ile Gln Phe
     50                  55                  60

GAA GGA AAA TAC AAT TGT ACC AAT CAA CGA TTC TTC GAC CTG GTA TCC     240
Glu Gly Lys Tyr Asn Cys Thr Asn Gln Arg Phe Phe Asp Leu Val Ser
 65                  70                  75                  80

CCA ACC AGG TCA GCA CAT TTC CAT CCG AAC ATT CAG GGA GCT AAA TCG     288
Pro Thr Arg Ser Ala His Phe His Pro Asn Ile Gln Gly Ala Lys Ser
                 85                  90                  95

AGC TCC GAC GTC AAG TCC TAT ATC GAC AAG GAC GGA GAT GTT CTT GAA     336
Ser Ser Asp Val Lys Ser Tyr Ile Asp Lys Asp Gly Asp Val Leu Glu
            100                 105                 110

TGG GGT ACT TTC CAG ATC GAC GGA CGA TCT GCT AGG GGA GGA CAA CAG     384
Trp Gly Thr Phe Gln Ile Asp Gly Arg Ser Ala Arg Gly Gly Gln Gln
        115                 120                 125

ACA GCC AAC GAC GCT TAC GCA AAG GCA ATT AAC GCA GGA AGT AAG TCG     432
Thr Ala Asn Asp Ala Tyr Ala Lys Ala Ile Asn Ala Gly Ser Lys Ser
    130                 135                 140

CAG GCT CTT GAT GTA ATT AAA GAA TTA GCG CCT AGA GAT TAC GTT CTA     480
Gln Ala Leu Asp Val Ile Lys Glu Leu Ala Pro Arg Asp Tyr Val Leu
145                 150                 155                 160

CAT TTT CAT AAT ATA AAT AGT AAT TTA GAT AAG GTT TTC CAG GTG CCT     528
His Phe His Asn Ile Asn Ser Asn Leu Asp Lys Val Phe Gln Val Pro
                165                 170                 175

CCG GCA CCT TAT GTT TCT CCT TTT TTA TCT TCT TCT TTC GAT CAA GTT     576
Pro Ala Pro Tyr Val Ser Pro Phe Leu Ser Ser Ser Phe Asp Gln Val
            180                 185                 190

CCT GAT GAA CTT GAA CAC TGG GTT TCC GAG AAC GTC ATG GAT GCC GCT     624
Pro Asp Glu Leu Glu His Trp Val Ser Glu Asn Val Met Asp Ala Ala
        195                 200                 205

GCG CGG CCT TGG AGA CCG GTG AGT ATA GTG ATT GAG GGT GAC AGC CGG     672
Ala Arg Pro Trp Arg Pro Val Ser Ile Val Ile Glu Gly Asp Ser Arg
    210                 215                 220
```

```
ACA GGA AAG ACA ACG TGG GCC CGT TCA TTA GGC CCA CAT AAT TAT TTG      720
Thr Gly Lys Thr Thr Trp Ala Arg Ser Leu Gly Pro His Asn Tyr Leu
225                 230                 235                 240

TGC GGC CAT CTT GAC CTC AGT CAA AAA GTA TAC AGC AAT AAT GCT TGG      768
Cys Gly His Leu Asp Leu Ser Gln Lys Val Tyr Ser Asn Asn Ala Trp
            245                 250                 255

TAT AAC GTC ATT GAT GAC GTC GAC CCG CAT TAT TTA AAA CAC TTT AAA      816
Tyr Asn Val Ile Asp Asp Val Asp Pro His Tyr Leu Lys His Phe Lys
                260                 265                 270

GAA TTT ATG GGG GCC CAA AGA GAT TGG CAA AGC AAC ACA AAG TAT GGC      864
Glu Phe Met Gly Ala Gln Arg Asp Trp Gln Ser Asn Thr Lys Tyr Gly
            275                 280                 285

AAG CCC ATT CAA ATT AAA GGA GGC ATT CCC ACT ATC TTC CTA TGC AAT      912
Lys Pro Ile Gln Ile Lys Gly Gly Ile Pro Thr Ile Phe Leu Cys Asn
        290                 295                 300

CCA GGC CCA CAA TCA TCA TTT AAA GAA TAT CTC GAC GAA GAA AAA AAT      960
Pro Gly Pro Gln Ser Ser Phe Lys Glu Tyr Leu Asp Glu Glu Lys Asn
305                 310                 315                 320

CAA GCA TTA AAA AAC TGG GCT ACT AAG AAT GCA ATC TTC GTC ACC ATC     1008
Gln Ala Leu Lys Asn Trp Ala Thr Lys Asn Ala Ile Phe Val Thr Ile
                325                 330                 335

CAC CAG CCA TTG TTC GCA GAT ACC AAT CAA AAT ACA ACA TCA CAT CGC     1056
His Gln Pro Leu Phe Ala Asp Thr Asn Gln Asn Thr Thr Ser His Arg
            340                 345                 350

CAA GAA GAG GCA AGT GAG GCG TAGATTTTCC CAAATAACAA ACCTACAAAC        1107
Gln Glu Glu Ala Ser Glu Ala
            355

ACCCACAAAC AAATTATTCT TCGTCATTCA TATCAACCAA C                       1148

(2) INFORMATION FOR SEQ ID NO:2:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Arg Ser Gly Arg Phe Ser Ile Lys Ala Lys Asn Tyr Phe Leu
1               5                   10                  15

Thr Tyr Pro Lys Cys Asp Leu Thr Lys Glu Asn Ala Leu Ser Gln Ile
            20                  25                  30

Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala Asn Asp Ala Tyr Ala Lys Ala Ile Asn Ala Gly Ser Lys Ser
    130                 135                 140

Gln Ala Leu Asp Val Ile Lys Glu Leu Ala Pro Arg Asp Tyr Val Leu
```

```
                    145                 150                 155                 160
His Phe His Asn Ile Asn Ser Asn Leu Asp Lys Val Phe Gln Val Pro
                165                 170                 175

Pro Ala Pro Tyr Val Ser Pro Phe Leu Ser Ser Phe Asp Gln Val
        180                 185                 190

Pro Asp Glu Leu Glu His Trp Val Ser Glu Asn Val Met Asp Ala Ala
            195                 200                 205

Ala Arg Pro Trp Arg Pro Val Ser Ile Val Ile Glu Gly Asp Ser Arg
        210                 215                 220

Thr Gly Lys Thr Thr Trp Ala Arg Ser Leu Gly Pro His Asn Tyr Leu
225                 230                 235                 240

Cys Gly His Leu Asp Leu Ser Gln Lys Val Tyr Ser Asn Asn Ala Trp
                245                 250                 255

Tyr Asn Val Ile Asp Asp Val Asp Pro His Tyr Leu Lys His Phe Lys
                260                 265                 270

Glu Phe Met Gly Ala Gln Arg Asp Trp Gln Ser Asn Thr Lys Tyr Gly
            275                 280                 285

Lys Pro Ile Gln Ile Lys Gly Gly Ile Pro Thr Ile Phe Leu Cys Asn
        290                 295                 300

Pro Gly Pro Gln Ser Ser Phe Lys Glu Tyr Leu Asp Glu Lys Asn
305                 310                 315                 320

Gln Ala Leu Lys Asn Trp Ala Thr Lys Asn Ala Ile Phe Val Thr Ile
                325                 330                 335

His Gln Pro Leu Phe Ala Asp Thr Asn Gln Asn Thr Thr Ser His Arg
            340                 345                 350

Gln Glu Glu Ala Ser Glu Ala
        355

(2) INFORMATION FOR SEQ ID NO:3:

(i) SEQUENCE CHARACTERISTICS:
            (A) LENGTH: 1150 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..1077

(xi) SEQUENCE DESCRIPTION: SEQ ID NO:3:

ATG CCA AGA TCA GGT CGT TTT AGT ATC AAG GCT AAA AAT TAT TTC CTT        48
Met Pro Arg Ser Gly Arg Phe Ser Ile Lys Ala Lys Asn Tyr Phe Leu
 1               5                  10                  15

ACA TAT CCC AAA TGT GAT TTA ACA AAA GAA AAT GCA CTT TCC CAA ATA        96
Thr Tyr Pro Lys Cys Asp Leu Thr Lys Glu Asn Ala Leu Ser Gln Ile
                20                  25                  30

ACA AAC CTA CAA ACA CCC ACA AAC AAA TTA TTC ATC AAA ATT TGC AGA       144
Thr Asn Leu Gln Thr Pro Thr Asn Lys Leu Phe Ile Lys Ile Cys Arg
            35                  40                  45

GAA CTA CAT GAA AAT GGG GAA CCT CAT CTC CAT ATT CTC ATC CAA TTC       192
Glu Leu His Glu Asn Gly Glu Pro His Leu His Ile Leu Ile Gln Phe
        50                  55                  60

GAA GGA AAA TAC AAT TGT ACC AAT CAA CGA TTC TTC GAC CTG GTA TCC       240
Glu Gly Lys Tyr Asn Cys Thr Asn Gln Arg Phe Phe Asp Leu Val Ser
65                  70                  75                  80

CCA ACC AGG TCA GCA CAT TTC CAT CCG AAC ATT CAG GGA GCT AAA TCG       288
```

```
                                        -continued

Pro Thr Arg Ser Ala His Phe His Pro Asn Ile Gln Gly Ala Lys Ser
                85                  90                  95

AGC TCC GAC GTC AAG TCC TAT ATC GAC AAG GAC GGA GAT GTT CTT GAA        336
Ser Ser Asp Val Lys Ser Tyr Ile Asp Lys Asp Gly Asp Val Leu Glu
            100                 105                 110

TGG GGT ACT TTC CAG ATC GAC GGA CGA TCT GCT AGG GGA GGA CAA CAG        384
Trp Gly Thr Phe Gln Ile Asp Gly Arg Ser Ala Arg Gly Gly Gln Gln
        115                 120                 125

ACA GCC AAC GAC GCT TAC GCA AAG GCA ATT AAC GCA GGA AGT AAG TCG        432
Thr Ala Asn Asp Ala Tyr Ala Lys Ala Ile Asn Ala Gly Ser Lys Ser
    130                 135                 140

CAG GCT CTT GAT GTA ATT AAA GAA TTA GCG CCT AGA GAT TAC GTT CTA        480
Gln Ala Leu Asp Val Ile Lys Glu Leu Ala Pro Arg Asp Tyr Val Leu
145                 150                 155                 160

CAT TTT CAT AAT ATA AAT AGT AAT TTA GAT AAG GTT TTC CAG GTG CCT        528
His Phe His Asn Ile Asn Ser Asn Leu Asp Lys Val Phe Gln Val Pro
                165                 170                 175

CCG GCA CCT TAT GTT TCT CCT TTT TTA TCT TCT TCT TTC GAT CAA GTT        576
Pro Ala Pro Tyr Val Ser Pro Phe Leu Ser Ser Ser Phe Asp Gln Val
            180                 185                 190

CCT GAT GAA CTT GAA CAC TGG GTT TCC GAG AAC GTC ATG GAT GCC GCT        624
Pro Asp Glu Leu Glu His Trp Val Ser Glu Asn Val Met Asp Ala Ala
        195                 200                 205

GCG CGG CCT TGG AGA CCG GTG AGT ATA GTG ATT GAG GGT GAC AGC CGG        672
Ala Arg Pro Trp Arg Pro Val Ser Ile Val Ile Glu Gly Asp Ser Arg
    210                 215                 220

ACA GGA GCG ACA ACG TGG GCC CGT TCA TTA GGC CCA CAT AAT TAT TTG        720
Thr Gly Ala Thr Thr Trp Ala Arg Ser Leu Gly Pro His Asn Tyr Leu
225                 230                 235                 240

TGC GGC CAT CTT GAC CTC AGT CAA AAA GTA TAC AGC AAT AAT GCT TGG        768
Cys Gly His Leu Asp Leu Ser Gln Lys Val Tyr Ser Asn Asn Ala Trp
                245                 250                 255

TAT AAC GTC ATT GAT GAC GTC GAC CCG CAT TAT TTA AAA CAC TTT AAA        816
Tyr Asn Val Ile Asp Asp Val Asp Pro His Tyr Leu Lys His Phe Lys
            260                 265                 270

GAA TTT ATG GGG GCC CAA AGA GAT TGG CAA AGC AAC ACA AAG TAT GGC        864
Glu Phe Met Gly Ala Gln Arg Asp Trp Gln Ser Asn Thr Lys Tyr Gly
        275                 280                 285

AAG CCC ATT CAA ATT AAA GGA GGC ATT CCC ACT ATC TTC CTA TGC AAT        912
Lys Pro Ile Gln Ile Lys Gly Gly Ile Pro Thr Ile Phe Leu Cys Asn
    290                 295                 300

CCA GGC CCA CAA TCA TCA TTT AAA GAA TAT CTC GAC GAA GAA AAA AAT        960
Pro Gly Pro Gln Ser Ser Phe Lys Glu Tyr Leu Asp Glu Glu Lys Asn
305                 310                 315                 320

CAA GCA TTA AAA AAC TGG GCT ACT AAG AAT GCA ATC TTC GTC ACC ATC       1008
Gln Ala Leu Lys Asn Trp Ala Thr Lys Asn Ala Ile Phe Val Thr Ile
                325                 330                 335

CAC CAG CCA TTG TTC GCA GAT ACC AAT CAA AAT ACA ACA TCA CAT CGC       1056
His Gln Pro Leu Phe Ala Asp Thr Asn Gln Asn Thr Thr Ser His Arg
            340                 345                 350

CAA GAA GAG GCA AGT GAG GCG TAGATACTTT CCCAAATAAC AAACCTACAA          1107
Gln Glu Glu Ala Ser Glu Ala
        355

ACACCCACAA ACAAATTATT CTTCGTCATT CATATCAACC AAC                       1150

(2) INFORMATION FOR SEQ ID NO:4:

(i) SEQUENCE CHARACTERISTICS:
          (A) LENGTH: 359 amino acids
          (B) TYPE: amino acid
```

(D) TOPOLOGY: linear (ii) MOLECULE TYPE: protein (xi) SEQUENCE DESCRIPTION: SEQ ID NO:4:

```
Met Pro Arg Ser Gly Arg Phe Ser Ile Lys Ala Lys Asn Tyr Phe Leu
 1               5                  10                  15

Thr Tyr Pro Lys Cys Asp Leu Thr Lys Glu Asn Ala Leu Ser Gln Ile
            20                  25                  30

Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala Asn Asp Ala Tyr Ala Lys Ala Ile Asn Ala Gly Ser Lys Ser
    130                 135                 140

Gln Ala Leu Asp Val Ile Lys Glu Leu Ala Pro Arg Asp Tyr Val Leu
145                 150                 155                 160

His Phe His Asn Ile Asn Ser Asn Leu Asp Lys Val Phe Gln Val Pro
                165                 170                 175

Pro Ala Pro Tyr Val Ser Pro Phe Leu Ser Ser Ser Phe Asp Gln Val
            180                 185                 190

Pro Asp Glu Leu Glu His Trp Val Ser Glu Asn Val Met Asp Ala Ala
        195                 200                 205

Ala Arg Pro Trp Arg Pro Val Ser Ile Val Ile Glu Gly Asp Ser Arg
    210                 215                 220

Thr Gly Ala Thr Thr Trp Ala Arg Ser Leu Gly Pro His Asn Tyr Leu
225                 230                 235                 240

Cys Gly His Leu Asp Leu Ser Gln Lys Val Tyr Ser Asn Asn Ala Trp
                245                 250                 255

Tyr Asn Val Ile Asp Asp Val Asp Pro His Tyr Leu Lys His Phe Lys
            260                 265                 270

Glu Phe Met Gly Ala Gln Arg Asp Trp Gln Ser Asn Thr Lys Tyr Gly
        275                 280                 285

Lys Pro Ile Gln Ile Lys Gly Gly Ile Pro Thr Ile Phe Leu Cys Asn
    290                 295                 300

Pro Gly Pro Gln Ser Ser Phe Lys Glu Tyr Leu Asp Glu Lys Asn
305                 310                 315                 320

Gln Ala Leu Lys Asn Trp Ala Thr Lys Asn Ala Ile Phe Val Thr Ile
                325                 330                 335

His Gln Pro Leu Phe Ala Asp Thr Asn Gln Asn Thr Thr Ser His Arg
            340                 345                 350

Gln Glu Glu Ala Ser Glu Ala
            355
```

(2) INFORMATION FOR SEQ ID NO:5:

(i) SEQUENCE CHARACTERISTICS:

(A) LENGTH: 1150 base pairs
(B) TYPE: nucleic acid
(C) STRANDEDNESS: double
(D) TOPOLOGY: linear (ii) MOLECULE TYPE: DNA (genomic)

(ix) FEATURE:
    (A) NAME/KEY: CDS
    (B) LOCATION: 1..1077

(xi) SEQUENCE DESCRIPTION: SEQ ID NO:5:

```
ATG CCA AGA TCA GGT CGT TTT AGT ATC AAG GCT AAA AAT TAT TTC CTT       48
Met Pro Arg Ser Gly Arg Phe Ser Ile Lys Ala Lys Asn Tyr Phe Leu
 1               5                  10                  15

ACA TAT CCC AAA TGT GAT TTA ACA AAA GAA AAT GCA CTT TCC CAA ATA       96
Thr Tyr Pro Lys Cys Asp Leu Thr Lys Glu Asn Ala Leu Ser Gln Ile
                20                  25                  30

ACA AAC CTA CAA ACA CCC ACA AAC AAA TTA TTC ATC AAA ATT TGC AGA      144
Thr Asn Leu Gln Thr Pro Thr Asn Lys Leu Phe Ile Lys Ile Cys Arg
            35                  40                  45

GAA CTA CAT GAA AAT GGG GAA CCT CAT CTC CAT ATT CTC ATC CAA TTC      192
Glu Leu His Glu Asn Gly Glu Pro His Leu His Ile Leu Ile Gln Phe
 50                  55                  60

GAA GGA AAA TAC AAT TGT ACC AAT CAA CGA TTC TTC GAC CTG GTA TCC      240
Glu Gly Lys Tyr Asn Cys Thr Asn Gln Arg Phe Phe Asp Leu Val Ser
 65                  70                  75                  80

CCA ACC AGG TCA GCA CAT TTC CAT CCG AAC ATT CAG GGA GCT AAA TCG      288
Pro Thr Arg Ser Ala His Phe His Pro Asn Ile Gln Gly Ala Lys Ser
                85                  90                  95

AGC TCC GAC GTC AAG TCC TAT ATC GAC AAG GAC GGA GAT GTT CTT GAA      336
Ser Ser Asp Val Lys Ser Tyr Ile Asp Lys Asp Gly Asp Val Leu Glu
                100                 105                 110

TGG GGT ACT TTC CAG ATC GAC GGA CGA TCT GCT AGG GGA GGA CAA CAG      384
Trp Gly Thr Phe Gln Ile Asp Gly Arg Ser Ala Arg Gly Gly Gln Gln
            115                 120                 125

ACA GCC AAC GAC GCT TAC GCA AAG GCA ATT AAC GCA GGA AGT AAG TCG      432
Thr Ala Asn Asp Ala Tyr Ala Lys Ala Ile Asn Ala Gly Ser Lys Ser
130                 135                 140

CAG GCT CTT GAT GTA ATT AAA GAA TTA GCG CCT AGA GAT TAC GTT CTA      480
Gln Ala Leu Asp Val Ile Lys Glu Leu Ala Pro Arg Asp Tyr Val Leu
145                 150                 155                 160

CAT TTT CAT AAT ATA AAT AGT AAT TTA GAT AAG GTT TTC CAG GTG CCT      528
His Phe His Asn Ile Asn Ser Asn Leu Asp Lys Val Phe Gln Val Pro
                165                 170                 175

CCG GCA CCT TAT GTT TCT CCT TTT TTA TCT TCT TCT TTC GAT CAA GTT      576
Pro Ala Pro Tyr Val Ser Pro Phe Leu Ser Ser Ser Phe Asp Gln Val
                180                 185                 190

CCT GAT GAA CTT GAA CAC TGG GTT TCC GAG AAC GTC ATG GAT GCC GCT      624
Pro Asp Glu Leu Glu His Trp Val Ser Glu Asn Val Met Asp Ala Ala
            195                 200                 205

GCG CGG CCT TGG AGA CCG GTG AGT ATA GTG ATT GAG GGT GAC AGC CGG      672
Ala Arg Pro Trp Arg Pro Val Ser Ile Val Ile Glu Gly Asp Ser Arg
            210                 215                 220

ACA GGA CAT ACC ACG TGG GCC CGT TCA TTA GGC CCA CAT AAT TAT TTG      720
Thr Gly His Thr Thr Trp Ala Arg Ser Leu Gly Pro His Asn Tyr Leu
225                 230                 235                 240

TGC GGC CAT CTT GAC CTC AGT CAA AAA GTA TAC AGC AAT AAT GCT TGG      768
Cys Gly His Leu Asp Leu Ser Gln Lys Val Tyr Ser Asn Asn Ala Trp
                245                 250                 255

TAT AAC GTC ATT GAT GAC GTC GAC CCG CAT TAT TTA AAA CAC TTT AAA      816
Tyr Asn Val Ile Asp Asp Val Asp Pro His Tyr Leu Lys His Phe Lys
```

-continued

```
              260                 265                 270
GAA TTT ATG GGG GCC CAA AGA GAT TGG CAA AGC AAC ACA AAG TAT GGC       864
Glu Phe Met Gly Ala Gln Arg Asp Trp Gln Ser Asn Thr Lys Tyr Gly
        275                 280                 285

AAG CCC ATT CAA ATT AAA GGA GGC ATT CCC ACT ATC TTC CTA TGC AAT       912
Lys Pro Ile Gln Ile Lys Gly Gly Ile Pro Thr Ile Phe Leu Cys Asn
    290                 295                 300

CCA GGC CCA CAA TCA TCA TTT AAA GAA TAT CTC GAC GAA GAA AAA AAT       960
Pro Gly Pro Gln Ser Ser Phe Lys Glu Tyr Leu Asp Glu Glu Lys Asn
305                 310                 315                 320

CAA GCA TTA AAA AAC TGG GCT ACT AAG AAT GCA ATC TTC GTC ACC ATC      1008
Gln Ala Leu Lys Asn Trp Ala Thr Lys Asn Ala Ile Phe Val Thr Ile
            325                 330                 335

CAC CAG CCA TTG TTC GCA GAT ACC AAT CAA AAT ACA ACA TCA CAT CGC      1056
His Gln Pro Leu Phe Ala Asp Thr Asn Gln Asn Thr Thr Ser His Arg
                340                 345                 350

CAA GAA GAG GCA AGT GAG GCG TAGATACTTT CCCAAATAAC AAACCTACAA         1107
Gln Glu Glu Ala Ser Glu Ala
                355

ACACCCACAA ACAAATTATT CTTCGTCATT CATATCAACC AAC                      1150
```

(2) INFORMATION FOR SEQ ID NO:6:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:6:

```
Met Pro Arg Ser Gly Arg Phe Ser Ile Lys Ala Lys Asn Tyr Phe Leu
 1               5                  10                  15

Thr Tyr Pro Lys Cys Asp Leu Thr Lys Glu Asn Ala Leu Ser Gln Ile
            20                  25                  30

Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala Asn Asp Ala Tyr Ala Lys Ala Ile Asn Ala Gly Ser Lys Ser
    130                 135                 140

Gln Ala Leu Asp Val Ile Lys Glu Leu Ala Pro Arg Asp Tyr Val Leu
145                 150                 155                 160

His Phe His Asn Ile Asn Ser Asn Leu Asp Lys Val Phe Gln Val Pro
                165                 170                 175

Pro Ala Pro Tyr Val Ser Pro Phe Leu Ser Ser Ser Phe Asp Gln Val
            180                 185                 190

Pro Asp Glu Leu Glu His Trp Val Ser Glu Asn Val Met Asp Ala Ala
        195                 200                 205
```

```
Ala Arg Pro Trp Arg Pro Val Ser Ile Val Ile Glu Gly Asp Ser Arg
    210                 215                 220

Thr Gly His Thr Thr Trp Ala Arg Ser Leu Gly Pro His Asn Tyr Leu
225                 230                 235                 240

Cys Gly His Leu Asp Leu Ser Gln Lys Val Tyr Ser Asn Asn Ala Trp
                245                 250                 255

Tyr Asn Val Ile Asp Asp Val Asp Pro His Tyr Leu Lys His Phe Lys
                260                 265                 270

Glu Phe Met Gly Ala Gln Arg Asp Trp Gln Ser Asn Thr Lys Tyr Gly
            275                 280                 285

Lys Pro Ile Gln Ile Lys Gly Gly Ile Pro Thr Ile Phe Leu Cys Asn
            290                 295                 300

Pro Gly Pro Gln Ser Ser Phe Lys Glu Tyr Leu Asp Glu Glu Lys Asn
305                 310                 315                 320

Gln Ala Leu Lys Asn Trp Ala Thr Lys Asn Ala Ile Phe Val Thr Ile
                325                 330                 335

His Gln Pro Leu Phe Ala Asp Thr Asn Gln Asn Thr Thr Ser His Arg
                340                 345                 350

Gln Glu Glu Ala Ser Glu Ala
            355

(2) INFORMATION FOR SEQ ID NO:7:

(i) SEQUENCE CHARACTERISTICS:
        (A) LENGTH: 1145 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: CDS
         (B) LOCATION: 1..1077

(xi) SEQUENCE DESCRIPTION: SEQ ID NO:7:

ATG CCA AGA TCA GGT CGT TTT AGT ATC AAG GCT AAA AAT TAT TTC CTT      48
Met Pro Arg Ser Gly Arg Phe Ser Ile Lys Ala Lys Asn Tyr Phe Leu
 1               5                  10                  15

ACA TAT CCC AAA TGT GAT TTA ACA AAA GAA AAT GCA CTT TCC CAA ATA      96
Thr Tyr Pro Lys Cys Asp Leu Thr Lys Glu Asn Ala Leu Ser Gln Ile
             20                  25                  30

ACA AAC CTA CAA ACA CCC ACA AAC AAA TTA TTC ATC AAA ATT TGC AGA     144
Thr Asn Leu Gln Thr Pro Thr Asn Lys Leu Phe Ile Lys Ile Cys Arg
         35                  40                  45

GAA CTA CAT GAA AAT GGG GAA CCT CAT CTC CAT ATT CTC ATC CAA TTC     192
Glu Leu His Glu Asn Gly Glu Pro His Leu His Ile Leu Ile Gln Phe
     50                  55                  60

GAA GGA AAA TAC AAT TGT ACC AAT CAA CGA TTC TTC GAC CTG GTA TCC     240
Glu Gly Lys Tyr Asn Cys Thr Asn Gln Arg Phe Phe Asp Leu Val Ser
 65                  70                  75                  80

CCA ACC AGG TCA GCA CAT TTC CAT CCG AAC ATT CAG GGA GCT AAA TCG     288
Pro Thr Arg Ser Ala His Phe His Pro Asn Ile Gln Gly Ala Lys Ser
                 85                  90                  95

AGC TCC GAC GTC AAG TCC TAT ATC GAC AAG GAC GGA GAT GTT CTT GAA     336
Ser Ser Asp Val Lys Ser Tyr Ile Asp Lys Asp Gly Asp Val Leu Glu
            100                 105                 110

TGG GGT ACT TTC CAG ATC GAC GGA CGA TCT GCT AGG GGA GGA CAA CAG     384
Trp Gly Thr Phe Gln Ile Asp Gly Arg Ser Ala Arg Gly Gly Gln Gln
        115                 120                 125
```

```
ACA GCC AAC GAC GCT TAC GCA AAG GCA ATT AAC GCA GGA AGT AAG TCG       432
Thr Ala Asn Asp Ala Tyr Ala Lys Ala Ile Asn Ala Gly Ser Lys Ser
        130                 135                 140

CAG GCT CTT GAT GTA ATT AAA GAA TTA GCG CCT AGA GAT TAC GTT CTA       480
Gln Ala Leu Asp Val Ile Lys Glu Leu Ala Pro Arg Asp Tyr Val Leu
145                 150                 155                 160

CAT TTT CAT AAT ATA AAT AGT AAT TTA GAT AAG GTT TTC CAG GTG CCT       528
His Phe His Asn Ile Asn Ser Asn Leu Asp Lys Val Phe Gln Val Pro
                165                 170                 175

CCG GCA CCT TAT GTT TCT CCT TTT TTA TCT TCT TCT TTC GAT CAA GTT       576
Pro Ala Pro Tyr Val Ser Pro Phe Leu Ser Ser Ser Phe Asp Gln Val
            180                 185                 190

CCT GAT GAA CTT GAA CAC TGG GTT TCC GAG AAC GTC ATG GAT GCC GCT       624
Pro Asp Glu Leu Glu His Trp Val Ser Glu Asn Val Met Asp Ala Ala
                195                 200                 205

GCG CGG CCT TGG AGA CCG GTG AGT ATA GTG ATT GAG GGT GAC AGC CGG       672
Ala Arg Pro Trp Arg Pro Val Ser Ile Val Ile Glu Gly Asp Ser Arg
210                 215                 220

ACA GGA AGG ACC ACG TGG GCC CGT TCA TTA GGC CCA CAT AAT TAT TTG       720
Thr Gly Arg Thr Thr Trp Ala Arg Ser Leu Gly Pro His Asn Tyr Leu
225                 230                 235                 240

TGC GGC CAT CTT GAC CTC AGT CAA AAA GTA TAC AGC AAT AAT GCT TGG       768
Cys Gly His Leu Asp Leu Ser Gln Lys Val Tyr Ser Asn Asn Ala Trp
                245                 250                 255

TAT AAC GTC ATT GAT GAC GTC GAC CCG CAT TAT TTA AAA CAC TTT AAA       816
Tyr Asn Val Ile Asp Asp Val Asp Pro His Tyr Leu Lys His Phe Lys
                260                 265                 270

GAA TTT ATG GGG GCC CAA AGA GAT TGG CAA AGC AAC ACA AAG TAT GGC       864
Glu Phe Met Gly Ala Gln Arg Asp Trp Gln Ser Asn Thr Lys Tyr Gly
            275                 280                 285

AAG CCC ATT CAA ATT AAA GGA GGC ATT CCC ACT ATC TTC CTA TGC AAT       912
Lys Pro Ile Gln Ile Lys Gly Gly Ile Pro Thr Ile Phe Leu Cys Asn
            290                 295                 300

CCA GGC CCA CAA TCA TCA TTT AAA GAA TAT CTC GAC GAA GAA AAA AAT       960
Pro Gly Pro Gln Ser Ser Phe Lys Glu Tyr Leu Asp Glu Glu Lys Asn
305                 310                 315                 320

CAA GCA TTA AAA AAC TGG GCT ACT AAG AAT GCA ATC TTC GTC ACC ATC      1008
Gln Ala Leu Lys Asn Trp Ala Thr Lys Asn Ala Ile Phe Val Thr Ile
                325                 330                 335

CAC CAG CCA TTG TTC GCA GAT ACC AAT CAA AAT ACA ACA TCA CAT CGC      1056
His Gln Pro Leu Phe Ala Asp Thr Asn Gln Asn Thr Thr Ser His Arg
            340                 345                 350

CAA GAA GAG GCA AGT GAG GCG TAGATCCCAA ATAACAAACC TACAAACACC         1107
Gln Glu Glu Ala Ser Glu Ala
            355

CACAAACAAA TTATTCTTCG TCATTCATAT CAACCAAC                            1145

(2) INFORMATION FOR SEQ ID NO:8:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:8:

Met Pro Arg Ser Gly Arg Phe Ser Ile Lys Ala Lys Asn Tyr Phe Leu
 1               5                  10                  15

Thr Tyr Pro Lys Cys Asp Leu Thr Lys Glu Asn Ala Leu Ser Gln Ile
            20                  25                  30
```

```
Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala Asn Asp Ala Tyr Ala Lys Ala Ile Asn Ala Gly Ser Lys Ser
130                 135                 140

Gln Ala Leu Asp Val Ile Lys Glu Leu Ala Pro Arg Asp Tyr Val Leu
145                 150                 155                 160

His Phe His Asn Ile Asn Ser Asn Leu Asp Lys Val Phe Gln Val Pro
                165                 170                 175

Pro Ala Pro Tyr Val Ser Pro Phe Leu Ser Ser Ser Phe Asp Gln Val
                180                 185                 190

Pro Asp Glu Leu Glu His Trp Val Ser Glu Asn Val Met Asp Ala Ala
        195                 200                 205

Ala Arg Pro Trp Arg Pro Val Ser Ile Val Ile Glu Gly Asp Ser Arg
210                 215                 220

Thr Gly Arg Thr Thr Trp Ala Arg Ser Leu Gly Pro His Asn Tyr Leu
225                 230                 235                 240

Cys Gly His Leu Asp Leu Ser Gln Lys Val Tyr Ser Asn Asn Ala Trp
                245                 250                 255

Tyr Asn Val Ile Asp Asp Val Asp Pro His Tyr Leu Lys His Phe Lys
                260                 265                 270

Glu Phe Met Gly Ala Gln Arg Asp Trp Gln Ser Asn Thr Lys Tyr Gly
        275                 280                 285

Lys Pro Ile Gln Ile Lys Gly Gly Ile Pro Thr Ile Phe Leu Cys Asn
290                 295                 300

Pro Gly Pro Gln Ser Ser Phe Lys Glu Tyr Leu Asp Glu Glu Lys Asn
305                 310                 315                 320

Gln Ala Leu Lys Asn Trp Ala Thr Lys Asn Ala Ile Phe Val Thr Ile
                325                 330                 335

His Gln Pro Leu Phe Ala Asp Thr Asn Gln Asn Thr Thr Ser His Arg
                340                 345                 350

Gln Glu Glu Ala Ser Glu Ala
        355

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gly Xaa Xaa Xaa Xaa Gly Lys Thr
1               5
```

```
(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Xaa Xaa Xaa Xaa Gly Lys Ser
1               5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Gly Xaa Gly Lys Thr
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Gly Xaa Gly Lys Ser
1               5

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCGGACAGGA GCGACCACGT GGGCC                                            25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CCGGACAGGA CATACCACGT GGGCC                                            25
```

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCGGACAGGA AGGACCACGT GGGCC                       25

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GTATCAAGGC TAGATCTTAA TTCCTTACAT ATCCC            35

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CCGGACAGGA AAGACCACGT GGGCC                       25

PHYTOPATHOGENIC GEMINIVIRUS RESISTANT TRANSGENIC PLANTS AND SEEDS AND METHODS FOR OBTAINING SAME BY INTRODUCTION OF MUTATED C1 GENE

BACKGROUND OF THE INVENTION

The present invention relates to transgenic plants that are resistant or tolerant to DNA viruses that are pathogenic in plants.

The invention relates more particularly to the seeds from these transgenic plants, which are capable of germinating into plants exhibiting this criterion of resistance or tolerance to phytopathogenic DNA viruses.

The invention also covers the methods of obtaining these plants and seeds.

DESCRIPTION OF THE RELATED ART

Phytopathogenic DNA viruses are essentially represented by single-stranded DNA viruses (ss) and double-stranded DNA viruses (ds).

The double-stranded DNA viruses mainly comprise the Badnaviruses and the Caulimoviruses.

The single-stranded DNA viruses mainly comprise the geminiviruses and other exotic ssDNA viruses.

Among these phytopathogenic DNA viruses, the geminiviruses have received particular study. These are plant viruses which have a considerable impact on agricultural production in many tropical and subtropical regions (Harrison, 1985). They are single-stranded circular DNA viruses, characterized by a structure that is unique in the world of viruses: a capsid in the shape of a double icosahedron (Francki et al., 1980). According to their genomic organization, a distinction is drawn between on the one hand the geminiviruses with a bipartite genome consisting of two DNA molecules A and B, each of about 2.8 kilobases (kb) (as in the case of the African Cassava Mosaic Virus (ACMV) and of the Tomato Golden Mosaic Virus (TGMV)), and on the other hand geminiviruses with a monopartite genome with a single DNA molecule of about 2.8 kb (as in the case of the Maize Streak Virus (MSV), the Wheat Dwarf Virus (WDV) and the Beet Curly Top Virus (BCTV)). Two subgroups have been identified, according to the transmission vector of the virus. Some geminiviruses are transmitted by the whitefly *Bemisia tabaci*, and until recently were all regarded as having a bipartite genome (ACMV, TGMV). The other geminiviruses are transmitted by leaf-hoppers (*Cicadulina* sp.) and they all have a monopartite genome (MSV, WDV and BCTV); for a review see Lazarowitz, 1992a.

The tomato yellow leaf curl virus (TYLCV) is an exception to this classification. Thus, although it is transmitted by *Bemisia tabaci*, its genome is monopartite (Kheyr-Pour et al., 1991; Navot et al., 1991). Only an isolate of TYLCV from Thailand has been described as having a bipartite genome (Rochester et al., 1990).

TYLCV is responsible for considerable damage to tomato crops, with losses of up to 50 to 60% (Allex et al., 1994). In this species, the characteristic symptoms include stunted appearance of the plant, leaf curl and yellowing, a bush-like appearance due to shortening of the internodes and arrest of floral growth. This disease, which already affects numerous regions (Mediterranean basin, Near and Middle East, extreme south of Asia, and Sahelian Africa), is spreading at present (Czosnek et al., 1990). Metropolitan France is spared for the present, but the French Antilles have been affected for two years (Hostachy and Allex, 1993).

Analysis of the viral genome sequence of TYLCV reveals the existence of six open reading frames (ORFs) able to code for products with size greater than 10 kDa. These ORFs are located both on the viral strand (ORFs V1 and V2) and on the complementary strand (ORFs C1, C2, C3 and C4) (Kheyr-Pour et al., 1991); see FIG. 1.

Transcription of the viral genome of the geminiviruses is bidirectional (Hanley-Bowdoin et al., 1988, Accotto et al., 1989). It takes place on either side of the intergenic region (IR), or region common to the two components of DNA of bipartite-genome viruses. The IR of about 200 nucleotides (nt) has a sequence of about 30 nt which could adopt a rod-loop structure. Using mutation analysis, this potential rod-loop structure was shown to be essential to replication of the viral DNA.

Replication of the viral genome passes through a double-stranded intermediate form, in the nuclei of the infected cells (Davies and Stanley, 1989). The presence, at the level of the potential rod-loop structure, of a highly-preserved nonanucleotide in all the geminiviruses (TAATATTAC) and similar to the cleavage site of gene product A of the uX174 bacteriophage, suggests a manner of replication according to the rolling circle model (Stenger et al., 1991; Saunders et al., 1991).

Gene C1 (or AL1) is the only viral gene that is essential to viral DNA replication (Elmer et al., 1988). All the other factors necessary to the replication of viral DNA are of cellular origin. Protein C1 does not have any sequence homology with the known DNA polymerases. Analysis of the amino-acid-deduced sequence of protein C1 reveals the existence of a consensus unit for fixing nucleoside triphosphates (NTP) or P-loop (standing for "phosphate loop"), GXXXGKT/S (SEQ ID NOS:9 and 10; G=glycine, K=lysine, T=threonine, S=Ser, X=any amino acid), which is preserved among the DNA and RNA helicases (Gorbalenya and Koonin, 1989). The roles of protein C1 in replication are not yet known. However, several publications are converging in the direction of multiple functions associated with protein C1. Protein AL1 of TGMV becomes fixed to a specific sequence of about 50 nt at the level of the common region (Fontes et al., 1992). This protein also possesses autoregulation activity by repression of its own transcription (Sunter et al., 1993). An ATPase activity as well as capacity for specific fixation to ATP in vitro have recently been demonstrated for protein C1 of TYLCV expressed in the form of fusion with glutathione-S-transferase (GST) in *Escherichia coli*. However, the possible role(s) of this ATPase activity in vivo has (have) not yet been elucidated. Moreover, an in vitro activity of cutting and joining of the protein GST-C1 of TYLCV at the level of the preserved nonanucleotide has been demonstrated. This dual activity of cleavage and joining in vitro is independent of the ATPase activity, since mutants that are defective in ATPase activity in vitro still possess the capacity to cleave and join viral DNA in vitro.

All tomato cultivars are sensitive to TYLCV. At present the fight against the virus is focused, without much success, on the vector *B. tabaci* by the use of insecticides and by protecting fields and greenhouses with very fine-meshed netting. It is therefore urgent to develop other more effective methods of control. Accordingly, natural resistance in wild species of tomato (*Lycopersicon chilense, L. hirsutum, L. peruvianum*) has been investigated with a view to introducing it in the domestic species *L. esculentum* (Zakay et al., 1990). A tolerance gene (absence of symptoms but replication of the viral DNA) was mapped by RFLP of chromosome 6 of *L. chilense* and called Ty-1 (Eshed et al., 1992). These introgression programmes are very long and exacting on account of the numerous backcrosses that are required. New strategies employing genetic engineering of plants have therefore been adopted alongside classical genetics. Two approaches have been used for obtaining transgenic plants that are tolerant or resistant to the geminiviruses (Frischmuth and Stanley, 1993). The first consists of expressing anti-sense sequences of the AL1 gene of TGMV in tobacco plants, thus leading to a reduction of the symptoms due to this virus (Day et al., 1991). The second approach is based on inhibition of movement of the ACMV in planta by expression of a recombinant defective movement protein of TGMV (von Arnim et al., 1992).

SUMMARY OF THE INVENTION

One of the aims of the present invention is to provide a new method of obtaining genetically altered plants that are resistant or tolerant to DNA viruses that are pathogenic in these plants.

Another aim of the present invention is to provide transgenic plants that are resistant or tolerant to DNA viruses.

Another aim of the present invention is to provide transgenic seeds that are capable of giving rise to the formation, by germination, of transgenic plants that are resistant or tolerant to DNA viruses.

BRIEF DESCRIPTION OF THE DRAWINGS

The invention is illustrated by means of the following figures:

FIG. 1: genomic organization of the Sardinia TYLCV (TYLCVsar), called "STYLCV" hereinafter, FIGS. 2A–2C: representation of the plasmids pTY Ala, His, Arg, of the plasmid pBMC1-S and of the plasmids pC1 Ala, His, Arg;

FIG. 3: mutations constructed in the genome of STYLCV;

FIG. 13: mutated nucleotide sequences C1* (derived by mutation of the sequence, namely ORF C1, coding for the protein C1 or Rep of STYLCV) coding for the mutated proteins $Rep^{K227A}$, $Rep^{K227H}$ and $Rep^{K227R}$, designated hereinafter by Ala, His and Arg mutation respectively.

DESCRIPTION OF THE PREFERRED EMBODIMENTS

Figure 4:
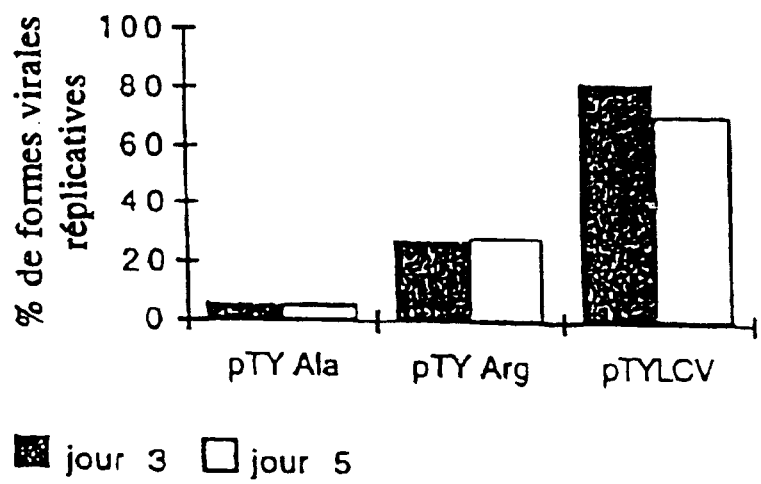
FIG. 4: replication of mutants at the NTP-binding site of STYLCV.

The invention relates to the use of nucleotide sequences derived by mutation (further designated mutated nucleotide sequences) of nucleotide sequences present in the genome of a DNA virus that is pathogenic in plants, the said mutated nucleotide sequences containing one (or more) mutation(s) such that it is (they are) capable of inducing a negative phenotype that is dominant for replication of the pathogenic virus, and/or the diffusion of this virus in a plant, and/or the distribution of this virus from one plant to other plants, notably by the intermediary of vectors such as insects, namely that the aforementioned mutated nucleotide sequences are capable of totally or partially inhibiting the replication and/or the diffusion and/or the distribution of the pathogenic virus, for obtaining (notably by the application of methods such as described later) transgenic plants that are resistant or tolerant to the aforementioned phytopathogenic DNA virus.

The mutated nucleotide sequences according to the invention correspond advantageously to all or part of the nucleotide sequences contained in the genome of the following phytopathogenic DNA viruses:

double-stranded DNA viruses, and more especially:
badnaviruses, such as CSSB (cacao swollen shoot badnavirus), DB (Dasheen badnavirus), CB (Commelina badnavirus), YIBSB (yam internal brown spot badnavirus), SPLCB (sweet potato leaf curl badnavirus), BSB (banana streak badnavirus), RTB (rice tungro badnavirus) and SB (sugarcane badnavirus);

caulimoviruses, such as PCSC (peanut chlorotic streak caulimovirus), CMC (cauliflower mosaic caulimovirus), SCMC (soybean chlorotic mottle caulimovirus), SPC (sweet potato caulimovirus), CVMC (cassava vein mosaic caulimovirus), and MMC (Mirabilis mosaic caulimovirus);

single-stranded DNA viruses, and more especially:
the geminiviruses, notably:
subgroup I (typical member MSV, maize streak virus), including the following isolates:
MSV, or maize streak virus,
CSMV (Chloris striate mosaic virus),
DSV (Digitaria streak virus),
MiSV (Miscanthus streak virus),
WDV (wheat dwarf virus),
PanSV-Ken (Panicum streak virus-Kenya),
SSV-N (sugarcane streak virus-Natal),
subgroup II (typical member BCTV, beet curly top virus), comprising the following isolates:
BCTV (beet curly top virus),
TPCTV (tomato pseudo-curly top virus),
BSDV (bean summer death virus),
TYDV (tobacco yellow dwarf virus),
TLRV (tomato leaf roll virus),
subgroup III (typical member BGMV, bean golden mosaic virus), comprising the following isolates:
BGMV (bean golden mosaic virus),
AbMV (Abutilon mosaic virus),
ACMV (African cassava mosaic virus),
CLCV (cotton leaf crumple virus),
EuMV (Euphorbia mosaic virus), HYVMV (honeysuckle yellow vein mosaic virus),
ICMV (Indian cassava mosaic virus),
MLCV (melon leaf curl virus),
MYMV (mungbean yellow mosaic virus),
PYMV (potato yellow mosaic virus),
SLCV (squash leaf curl virus),
TGMV (tomato golden mosaic virus),
TLCV (tomato leaf curl virus), notably TLCV-Aus and TLCV-Ind for Tomato leaf curl virus Australia and India respectively,
TYDV (tomato yellow dwarf virus),
TYLCV (tomato yellow leaf curl virus), notably STYLCV, for Sardinia TYLCV, including subsets, notably STYLCV-Sp (Spain), such as STYLCV-Sp-Murcia, STYLCV-Si (Sicily) or ITYLCV, for Israel TYLCV, including in particular the subsets ITYLCV-Eg (Egypt) and ITYLCV-Jo (Jordan),
ThTYLCV (Thailand TYLCV),
AToLCV (Australian tomato leaf curl virus),
IToLCV (Indian tomato leaf curl virus), including in particular the subspecies IToLCV-ND (New Delhi) and IToLCV-Bg (Bangalore),
TYMV (tomato yellow mosaic virus),
TomGV (tomato geminivirus MX3),
ToLCrV (tomato leaf crumple virus),
ToMoV-Flo (tomato mottle virus Florida),
"Chino del Tomate" virus,
WCSV (watermelon chlorotic stunt virus),
CLCV (cotton leaf curl virus),
CGMV (cowpea golden mosaic virus),
EYMV (eggplant yellow mosaic virus),
BCaMV (bean calico mosaic virus MoV2),
PhVCMV (bean calico mosaic virus P. vulgaris),
BDMV (bean dwarf mosaic virus),
PepGV (pepper geminivirus MX1),
PHV (pepper huasteco virus),
BYVMV (bhendi (okra) yellow vein mosaic virus),
CYVMV (croton yellow vein mosaic virus),
HYMV (Horsegram yellow mosaic virus),
DYWV (Dolichos yellow mosaic virus),
PMTV-T (pepper mild tigre virus-T),
SGMV (Serrano golden mosaic virus),
JMV (Jatropa mosaic virus),
LIYV (lettuce infectious yellow virus).

exotic single-stranded DNA viruses, and more particularly the small isometric viruses (containing 1 to 7 genomic components), such as SCSV (subterranean clover stunt virus, described by Chu and Helms in Virology 167, 38–48, 1988), CFDV (coconut foliar decay virus, described by Kohde et al., in Virology 176, 648–651, 1990), FBNYV (Faba bean necrotic yellow virus, described by Katal et al., in Ann. Appl. Biol., 123, 628–647, 1993), MVDV (milk vetch dwarf virus, described by Sano et al., in Abstr. 6th Plant Path. Congress, Montreal, pp. 305, Abst. 17.2.27, 1993), and BBTV (banana bunchy top virus, described by Harding et al., J. Gen. Virol., 74, 323–328, 1993).

For a review of phytopathogenic DNA viruses, especially single-stranded, which have nucleotide sequences from which it is possible to derive, by mutation, the nucleotide sequences of the invention, reference may be made to the following works:

"Classification and Nomenclature of Viruses", Fifth Report of the International Committee on Taxonomy of Viruses, edited by Francki, Fauquet, Knudson and Brown; Archives of Virology, Supplementum 2, Springer-Verlag Vienna, New York, 1991, "Viruses of Tropical Plants", Alan Brunt, Karen Crabtree and Adrian Gibbs, 1990, edited by C.A.B. International, Wallingford, Oxon., OX10 8DE, UK, "Virus Taxonomy, the VIth Report of the ICTV"; Murphy F. A., Fauquet C. M., Bishop D. H. L, Ghabrial S. A., Jarvis A. W., Martelli G. P., Mayo M. A., Summers M. D. (eds.) (1995), Springer-Verlag, Vienna, N.Y., pp. 570.

The mutated nucleotide sequences according to the invention, characterized by a negative phenotype that is dominant for the replication and/or diffusion and/or distribution of a phytopathogenic DNA virus, are selected advantageously among those that are non-pathogenic and capable of inhibiting totally or partially the replication and/or diffusion and/or distribution of the said pathogenic virus, when these mutated nucleotide sequences are cotransfected with the said pathogenic virus in plant cells, especially in protoplasts of plants that are sensitive to the phytopathogenic viruses in question.

The mutated nucleotide sequences according to the invention are chosen advantageously among those that are capable of totally or partially inhibiting the replication of the said pathogenic virus, notably in the aforementioned conditions of cotransfection of protoplasts.

The invention aims more particularly at the aforementioned use of mutated nucleotide sequences coding for one (or more) protein(s) capable of totally or partially inhibiting the replication of the said pathogenic virus.

The aforementioned mutated nucleotide sequences are chosen advantageously among those coding for one (or more) protein(s) possessing a negative phenotype that is dominant for the replication of the said pathogenic virus, especially when the vectors, such as plasmids containing these mutated nucleotide sequences integrated in their genome, as well as the elements necessary for the transcription of the latter, notably an appropriate promoter, are cotransfected with the said pathogenic virus, or with gene structures, such as plasmids, containing the genome of the said pathogenic virus, in protoplasts or any other cell or medium favourable to their replication.

The invention relates more particularly to the aforementioned use of mutated nucleotide sequences that have a negative phenotype that is dominant for the replication of phytopathogenic DNA viruses, and which are able to code for one (or more) mutated protein(s) corresponding to one (or more) protein(s) that are essential for replication of the said virus, or corresponding to a fragment of this (or these) protein(s) that is essential for the replication of the virus, and contains one (or more) mutation(s).

Advantageously, the mutated nucleotide sequences according to the invention are capable of coding for a mutated protein corresponding to a protein which, normally in a virus, is capable of:

binding specifically to the nucleotide sequences of the genome of the virus, notably in the intergenic region (IR) as defined above in the case of the geminiviruses, and/or repressing the transcription of its own gene, namely the gene coding for this gene, and/or exerting a specific endonuclease action capable of splitting and binding the viral genome at the level of its replication origin, in order to initiate and terminate DNA replication, and/or possessing NTPase activity (i.e. hydrolysis of nucleoside triphosphates) necessary for replication of the viral genome, and/or being phosphorylated by the kinases of plants, or corresponding to any fragment of this protein capable of possessing at least one of the aforementioned properties, the said protein containing one (or more) mutation(s).

The mutated nucleotide sequences according to the invention are chosen more particularly among those coding for a mutated protein that is inactive for virus replication, in contrast to the active protein to which it corresponds, this latter being essential for viral replication.

In particular, the mutated proteins according to the invention do not possess at least one of the aforementioned properties of the protein from which they are derived by mutation.

The invention relates more particularly to the aforementioned use of mutated nucleotide sequences coding for a mutated protein derived from protein Rep (further designated protein C1 or AL1) with a molecular weight of about 40 kDa, which is essential for replication of the genome of the geminiviruses (especially those described above), and possessing at least one of the aforementioned properties.

Advantageously, the mutated protein according to the invention lacks, totally or partly, the NTPase activity of the protein from it is derived, especially ATPase activity of the Rep protein of the geminiviruses from which it is derived.

Such a mutated protein, without any NTPase activity or with insufficient to permit viral replication, is coded by a mutated nucleotide sequence, advantageously obtained by substitution and/or suppression of one (or more) nucleotide (s) belonging to nucleotide chains coding for all or part of the sites of fixation of nucleoside triphosphate within the genome of the phytopathogenic virus whose replication we wish to inhibit, and/or by addition of one (or more) nucleotide(s) within the aforementioned nucleotide chains.

Advantageously, the mutation(s) effected on the aforementioned nucleotide chains leads (lead) to:

substitution and/or suppression of at least one of the amino acids underlined in one of the following two peptide sequences corresponding to sites of fixation of NTPs located on one (or more) viral protein(s) essential for replication, and more particularly the protein Rep:

—Gly-X-X-X-X-Gly-Lys-Thr/Ser (SEQ ID NOS:9 and 10) <25–100> Asp/Glu-Asp/Glu—

—Gly-X-Gly-Lys-Thr/Ser (SEQ ID NOS:11 and 12) <25–100> Asp/Glu-Asp/Glu—

<25–100> representing a chain from about 25 to about 100 of any amino acids,

X representing any amino acid, and/or the addition of one (or more) amino acid(s) at one (or more) site(s) of the aforementioned peptide sequences.

Advantageously, the mutation is effected by substitution of the lysine shown in the aforementioned peptide sequences, especially by alanine, arginine or histidine, and advantageously by alanine.

The invention relates more particularly to the use of the mutated nucleotide sequence coding for an inactive protein C1 corresponding to the active protein C1 of the geminiviruses, in which the lysine located between positions 220 and 235 of the said active protein C1 is replaced by alanine, arginine or histidine, to obtain plants that are resistant or tolerant to the geminiviruses.

The invention also relates more particularly to the use of mutated nucleotide sequences coding for an inactive protein C1 corresponding to the active protein C1 of the various isolates of the TYLC virus, such as the nucleotide sequences C1* shown in FIG. 13, in which the lysine at position 227 is replaced by alanine, arginine or histidine (with the exception of an Israeli isolate of the TYLC virus (ITYLCV) for which it would appear that the lysine in question is at position 225), for obtaining plants, especially tomatoes, that are resistant or tolerant to TYLC viruses.

Preferably, the aforementioned inactive protein C1 of the geminiviruses, especially of TYLC viruses, corresponds to the active protein C1, in which the lysine, located at one of the positions stated above, is replaced by an alanine.

The invention also relates to the use of at least one mutated nucleotide sequence as defined above, for the transformation of plant cells in order to obtain transgenic plants that are resistant or tolerant to the phytopathogenic DNA viruses.

By transgenic plants that are resistant to the phytopathogenic DNA viruses, we mean any plant in which, after infection by the said viruses, we do not detect, on the one hand, the pathologic symptoms characteristic of infection of a non-transgenic plant that is sensitive to the said viruses, and on the other hand the DNA of the said viruses within the cells of the said transgenic plants.

By transgenic plants that are tolerant to the phytopathogenic DNA viruses, we mean any plant in which, after infection by the said viruses, we do not detect the pathologic symptoms characteristic of infection of a non-transgenic plant that is sensitive to the said viruses, but in which the DNA of the said viruses can be detected in the cells of the said transgenic plants (in smaller quantities than in the case of infection of a plant that is sensitive to these viruses).

The mutated nucleotide sequences according to the invention are used advantageously for the transformation of protoplasts, or for the construction of vectors, such as plasmids, or for the transformation of bacteria such as *Agrobacterium tumefaciens*, which in their turn are capable of transforming plant cells.

The invention also relates to the aforementioned use of any mutated nucleotide sequence such as described above, derived by mutation of a nucleotide sequence present in the genome of a phytopathogenic DNA virus belonging to a defined family, such as the family of the geminiviruses, for obtaining transgenic plants that are resistant or tolerant to one or more viral sub-species and/or species belonging to this same family, and more particularly to one or more viral sub-species and/or species belonging to a same subgroup within this family, such as subgroup III, or belonging to a same member of a subgroup defined within this family, such as the TYLCVs.

In this connection, the invention relates more particularly to the aforementioned use of the mutated nucleotide sequence coding for an inactive protein C1 corresponding to the active protein C1 of the species STYLCV, in which the lysine at position 227 is replaced by alanine, arginine or histidine (as shown in FIG. 13), for obtaining plants, especially tomatoes, that are resistant or tolerant to the geminiviruses such as those belonging to the TYLCVs, especially to the viruses such as STYLCV and ITYLCV, especially ITYLCV-Jo, or non-TYLCV geminiviruses, especially ACMV or BGMV.

The invention also relates to any method of obtaining transgenic plants, especially tomatoes, that are resistant or tolerant to the phytopathogenic DNA viruses, characterized in that it comprises a stage of transformation of plant cells, by means of at least one mutated nucleotide sequence according to the invention, if necessary inserted in a vector or a bacterium as defined above, followed by regeneration of the plants starting from the cells thus transformed.

By way of illustration, a method such as described above consists of introducing a mutated nucleotide sequence according to the invention into a plant cell, especially a protoplast, if necessary by means of a vector (such as a plasmid), the transgenic plant being obtained by division of the cells thus transformed (method using naked DNA).

Another method consists of transforming plant cells by means of bacteria such as *Agrobacterium tumefaciens*, themselves transformed by at least one mutated nucleotide sequence according to the invention, especially following the technique of coculture or of leaf discs.

For a review of the techniques that can be employed for obtaining transgenic plants of the invention, one may refer to the article by Potrykus which appeared in Biotechnology, June 1990, 535–542.

The method according to the invention is carried out advantageously by transformation of the cells of a fragment of a plant, especially leaf discs, by means of bacteria *Agrobacterium tumefaciens*, transformed by a vector such as defined above, followed by the regeneration of the plants starting from the cells thus transformed, especially starting from buds formed at the periphery of the aforementioned leaf discs.

The invention also relates to the transgenic cells of plants possessing a heterologous DNA that is stably integrated in their genome, the said heterologous DNA containing, if necessary, a promoter recognized by the polymerases of the said plant cells, the said mutated nucleotide sequence being capable of totally or partially inhibiting the replication and/or the diffusion and/or the distribution of phytopathogenic DNA viruses, especially capable of coding, under the control of the said promoter, for a protein that is able to inhibit totally or partially the replication and/or the diffusion and/or the distribution of phytopathogenic DNA viruses within the said altered cells, the cells of *Nicotiana tabacum* cultivar BY2 (bright yellow 2, described by Nagata et al., 1992) being excluded.

The invention relates more particularly to the cells of plants as defined above, which can be regenerated into a transgenic plant that is resistant or tolerant to one or more strains of phytopathogenic DNA viruses, and capable of producing seeds, which are themselves resistant or tolerant to the said viruses.

Advantageously, the plant cells according to the invention are transformed according to a method such as described above.

The invention also relates to the transgenic seeds possessing a heterologous DNA stably integrated in the genome of their cells, the said heterologous DNA containing if necessary a promoter recognized by the polymerases of the said cells, and at least one mutated nucleotide sequence such as defined above, the said mutated nucleotide sequence being capable of inhibiting totally or partially the replication and/or diffusion and/or distribution of phytopathogenic DNA viruses, especially capable of coding, under the control of the said promoter, for a protein that is able to inhibit, totally or partially, the replication and/or diffusion and/or distribution of phytopathogenic viruses within the said transformed cells.

Advantageously, the seeds according to the invention are capable of germinating into a plant that is resistant or tolerant to the phytopathogenic DNA viruses, and more particularly to those defined above.

Preferably, the seeds according to the invention are transformed by a method such as described above.

The invention also relates to transgenic plants that are resistant or tolerant to phytopathogenic DNA viruses containing a heterologous DNA stably integrated in the genome of their cells, the said heterologous DNA containing if necessary a promoter that is recognized by the polymerases of the said plant cells, and at least one mutated nucleotide sequence as defined above, the said mutated nucleotide sequence being capable of inhibiting totally or partially the replication and/or diffusion and/or distribution of phytopathogenic DNA viruses, especially capable of coding, under the control of the said promoter, for a protein that is able to inhibit, totally or partially, the replication and/or diffusion and/or distribution of phytopathogenic viruses within the said transformed cells, the plants of *Nicotiana benthamiana* thus transformed being excluded.

Advantageously, the plants according to the invention are capable of producing seeds that are resistant to the phytopathogenic DNA viruses.

The invention relates more particularly to the aforementioned plants, as obtained by the application of a method as described above.

The transgenic plants according to the invention, resistant or tolerant to the phytopathogenic DNA viruses, especially to at least one of the DNA viruses described above, as obtained by transformation of their cells with at least one nucleotide sequence mutated according to the invention, are chosen advantageously among the following plants: Ageratum spp., especially *Ageratum conyzoides*, Arabidopsis spp., especially *Arabidopsis thaliana*, Arachis spp., especially *Arachis hypogea*, Asparagus spp., especially *Asparagus officinalis*, Avena spp., especially *Avena sativa* and *Avena byzantina*, Beta spp., especially *Beta vulgaris*, Brassica spp., especially *Brassica oleracea* vars *capitata, Brassica napus* and *Brassica rapa*, Cajanus spp., especially *Cajanus cajan*, Cannabis spp., especially *Cannabis sativa*, Capsicum spp., especially *Capsicum annuum*, Castanospermum spp., especially *Castanospermum australe*, Citrullus spp., especially *Citrullus colocynthis* and *Citrullus lanatus*, Cocos spp., especially *Cocos nucifera*, Cola spp., especially *Cola chlamydantha* and *Cola gigantea* var. *glabrescens*, Croton spp., especially *Croton lobatus*, Cucumis spp., especially *Cucumis melo* var. *cantalupensis* and *Cucumis melo*, Cucurbita spp., especially *Cucurbita maxima, Cucurbita moschata*, and *Cucurbita pepo*, Cynanchum spp., especially *Cynanchum acutum*, Datura spp., especially *Datura stramonium*, Dioscorea spp., especially *Dioscorea alata*, Euphorbia spp., especially *Euphorbia fulgens, Euphorbia heterphylla, Euphorbia peplus* and *Euphorbia pulcherrima*, Glycine spp., especially *Glycine max* and *Glycine hispida*, Gossypium spp., especially *Gossypium barbadense, Gossypium hirsutum, Gossypium thurberi* and *Gossypium herbaceum*, Helianthus spp, especially *Helianthus annuus*, Hibiscus spp., especially *Hibiscus cannabinus, Hibiscus esculentus* and *Hibiscus sabdariffa*, Hordeum spp., especially *Hordeum vulgare* and *Hordeum distichon*, Indigofera spp., especially *Indigofera hirsuta*, Ipomoea spp., especially *Ipomoea batatas*, Jatropha spp., especially *Jatropha gossypifolia, Jatropha multifida* and *Jatropha podagrica*, Lablab spp., especially *Lablab purpureus*, Linum spp., especially *Linum usitatissimum*, Lonicera spp., especially *Lonicera japonica*, Lycopersicon spp., especially *Lycopersicon esculentum, Lycopersicon hirsutum* and *Lycopersicon pimpinellifolium*, Macroptilium spp., especially *Macroptilium lathyroides*, Macrotyloma spp., especially *Macrotyloma uniflorum*, Malva spp., especially *Malva parviflora*, Malvastrum spp., especially *Malvastrum coromandelianum*, Manihot spp., especially *Manihot esculenta* and *Manihot glaziovii*, Medicago spp., especially *Medicago sativa*, Musa spp., especially *Musa sapientum*, Nicotiana spp., especially *Nicotiana tabacum*, Oryza spp., especially *Oryza sativa*, Phaseolus spp., especially *Phaseolus acutifolius, Phaseolus lunatus* and *Phaseolus vulgaris*, Pisum spp., especially *Pisum sativum*, Raphanus spp., especially *Raphanus sativus*, Saccharum spp., especially *Saccharum officinarum*, Secale spp., especially *Secale cereale*, Sida spp., especially *Sida rhombifolia*, Solanum spp., especially *Solanum melongena* and *Solanum tuberosum*, Sorghum spp., especially *Sorghum bicolor* and *Sorghum vulgare*, Spinacia spp., especially *Spinacia oleracea*, Theobroma spp., especially *Theobroma cacao*, the Triticales (wheat×rye hybrids), Triticum spp., especially *Triticum aestivum, Triticum durum* and *Triticum vulgare*, Vicia spp., especially *Vicia faba* and *Vicia sativa*, Vigna spp., especially *Vigna angularis, Vigna mungo, Vigna radiata* and *Vigna unguiculata*, Vitis spp., especially *Vitis vinifera*, Zea spp., especially *Zea mays*.

The invention will be further illustrated by the following detailed description of obtaining *N. benthamiana* and transgenic tomatoes that are resistant to infection by the TYLCVs, and more particularly by the STYLCVs and the ITYLCVs.

I) OBTAINING DOMINANT NEGATIVE MUTANTS IN THE NTP-BINDING SITE OF PROTEIN C1 OF TYLCV, A GEMINIVIRUS

A) MATERIAL AND TECHNIQUES a) Directed Mutagenesis pTYLCV is an infectious clone of the Sardinia isolate of TYLCV (STYLCV) in which the entire viral genome is cloned at the SstI site of the vector pUC118. Directed mutagenesis has been carried out on this clone, producing the plasmids pTYAla, pTYHis, pTYArg; respectively bearing the mutation corresponding to change of $K^{227}$ to A, H and R (FIG. 2).

Principle (Kunkel, 1985): A mutagenic oligonucleotide is hybridized to uridinylated single-stranded circular DNA submitted to mutagenesis. Synthesis of the second strand is carried out in vitro, then counter-selection of the uridinylated strand is effected by transformation in *E. coli* and repair of the double-stranded hybrid in vivo. The in vitro stage is carried out in the presence of restriction fragments covering the plasmid, so as to minimize the length of the neosynthesized complementary strand, which reduces the risks of introduction of new mutations.

1/—Obtaining the uridinylated single-stranded DNA:

The *E. coli* strain BW313 (Hfr lysA dut-ung-thi-1 recA spoT1), infected by the phage helper M13K07, is transformed by the plasmid to be mutagenized (pTYLCV). These bacteria then produce the uridinylated single-stranded DNA, the bacterium being deficient for the functions dUTPase and Uracile-N-Glycosilase, and encapsidated in single-stranded form on account of the functions coded by the phage M13K07 and to their action in trans on the replication origin of M13 contained in pUC118. The "phagemids" obtained are collected by a first centrifugation of the bacterial culture (10,000 rpm, 10 min), treatment of the supernatant with PEG 8000 20% and NaCl 2.5M (300 ml/ml), followed by a second centrifugation (6000 rpm, 20 min). The proteins are extracted by treatment with phenol/chloroform and the DNA is precipitated with ethanol (Sambrook et al., 1989).

2/—Hybridization with the mutagenic oligonucleotide and synthesis of the second strand:

The sequence of the oligonucleotides used is as follows:
mutation K to A: CCGGACAGGA<u>GC</u>GAC(<u>C</u>ACGTG)GGCC (SEQ ID NO:13).
mutation K to H: CCGGACAGGA<u>CA</u><u>T</u>AC(<u>C</u>ACGTG)GGCC (SEQ ID NO:14).
mutation K to R: CCGGACAGGAA<u>G</u>GAC(<u>C</u>ACGTG)GGCC (SEQ ID NO:15).

The parentheses indicate the positioning of the new restriction site PmlI.

Restriction fragments of the pTYLCV as well as the phosphorylated oligonucleotide (in molar excess of 25 relative to the corresponding restriction fragment) are hybridized on the uridinylated single-stranded DNA. The second strand is then synthesized (Klenow 10 units, Ligase 800 units, ATP 500 μM, dNTPs 500 μM, Tris 10 mM, MgCl$_2$ 5 mM, DTT 500 μM). We then transform an *E. coli* strain DH5α (supE44 ΔlacU169 (Φ80lacZDM15) hsdR17 recA1 endA1 gyrA96 thi-1 relA1) which will repair the DNA by degrading the uridinylated strand preferentially. The newly synthesized strand uses, as matrix, the complementary strand containing the mutation, which thus introduces it on the two strands.

b) Expression Cassettes of the Mutated ORF C1

The high-level expression of the mutated C1 proteins is accomplished by sub-cloning of the fragments bearing the mutation in the plasmid pBMC1-S, by making the ORF C1 dependent on a strong promoter, derived from the promoter 35S of the cauliflower mosaic virus (CaMV). The plasmid pBMC1-S contains the ORF of C1 cloned in a non-replicating vector shown in FIG. 2.

The site SstI$_{2860}$ was destroyed from this vector by the DNA polymerase of the phage T7. The HindIII-ScaI fragment, in which the SstI site is suppressed, is substituted to the corresponding HindIII-ScaI fragment in pBMC1-S: we thus obtain the plasmid pBMC1-S(SstI). Next, the SstI$_{365}$-BamHI$_{1170}$ fragment of this last plasmid was replaced by a fragment SstI-BglII of pTYAla, pTYHis, or pTYArg giving the plasmids pC1Ala, pC1His and pC1Arg respectively. We then create a new site at position 1170, cleavable by MboI or BstYI (FIG. 2).

c) Determintation of the Sequence of the Mutants Obtained

The technique of chain termination (Sanger et al., 1977; Sanger, 1981) (Kit Pharmacia-T7 Sequencing kit) was employed with, as matrix, the double-stranded DNA obtained by maxipreparation of plasmidic DNA (Sambrook et al., 1989). The reactions are deposited on a denaturing gel of acrylamide 6% for which a thickness gradient is effected (0.2 mm at the top and 0.6 mm at the bottom of the plates) so as to have good resolution of the bands on a larger part of the gel. Migration is effected in TBE buffer at 2000 V, with a thermostating device for maintaining the plates at 50° C., which gives a more even migration.

d) Cell Line and Preparation of Protoplasts

The cell line BY2 is a cell suspension derived from *Nicotiana tabacum* L cv Bright Yellow 2 (Kato et al., 1972; Nagata et al., 1992). It is diluted (2:100) every 7 days in a medium derived from the Murashige & Skoog medium (Sigma) supplemented with KH$_2$PO$_4$ (200 mg/l), myo-inositol (100 mg/l), thiamine-HCl (1 mg/l), saccharose (30 g/l), 2,4-D (0.2 mg/l), MES (2 g/l), pH 5.8. The culture is stirred continuously (130 rpm) at 26° C. in the dark.

For preparing the protoplasts, the cells from a 100 ml suspension of three to four days (inoculation of 2 to 3 ml in 100 ml) are collected by filtration, washed in 0.4 M mannitol and then transferred to 50 ml of the following enzyme solution: 1% Cellulase Onozuka RS, 0.1% Pectolyase, 0.4 M mannitol, pH 4.5 to 5.5. Digestion of the cell wall is effected at 28° C., with stirring (60 rpm) and in the dark. A microscope is used for checking that protoplasts have been obtained (1 to 2 h) (appearance of spherical cells). The protoplasts are then collected by centrifugation (100 g, 2 min), washed, counted in a Fuchs-Rosenthal cell and reabsorbed in MaMg medium (450 mM mannitol, 15 mM $MgCl_2$, 0.1% MES, pH 5.6) to the final density of $2.10^6$ protoplasts in 300 ml.

e) Transfection of the Protoplasts

Each transfection is effected with $2.10^6$ protoplasts and 15 mg of DNA (circular plasmid or double-stranded linear viral DNA). The DNA/protoplasts mixture is incubated for 20 min with 600 ml of PEG 1500 at 25% in the following solution: 0.1 M $MgCl_2.6H_2O$; 0.45 M mannitol, 0.02 M Hepes, pH 6. The protoplasts are then rinsed, absorbed in 10 ml of K3 medium (Nagy et al., 1976) and transferred to two 5.5 cm dia. Petri dishes. The transfected protoplasts are incubated at 28° C. in the dark without stirring and are collected after 3 and 5 days of culture.

f) Extraction of Total DNA from the Transfected Cells

The cells are collected by centrifugation (100 g, 5 min), washed and resuspended in 300 µl of extraction buffer (0.1 M NaCl, 0.1 M Tris-HCl pH8, 50 mM EDTA, 0.5% SDS) then left at −20° C.

Then they are pulverized in this buffer (Heidolph pulverizer). The proteins are extracted by treatment with phenol-chloroform (Sambrook et al., 1989) and the nucleic acids are precipitated from ethanol (Sambrook et al., 1989). The DNAs are absorbed in TE buffer and their concentration is determined from the optical density measured at 260 nm.

g) Electrophoresis, Transfer onto a Membrane and Hybridization of the Extracted DNAs Electrophoresis on 1% agarose gel is carried out without ethidium bromide, depositing 10 µg DNA per well. Migration conditions are as follows: 30 min at 60 V then about 16 hours at 25 V, in TBE buffer. The gel is depurinated in the presence of 0.25 N HCl and treated for alkaline transfer on Hybond-N membrane (Amersham). The probe used corresponds to the total genome of STYLCV. Labelling with $^{32}P$ is obtained by random priming (Kit Amersham Megaprime).

h) Extraction of Proteins and Neomycin Phosphotransferase Activity Test

The method employed was derived from the method described by Reiss et al., 1984.

NPT II activity is detected in situ on a gel of proteins that are not denatured by the phosphorylation of kanamycin to $[\gamma\text{-}^{32}P]$ ATP.

The protoplasts (half a Petri dish) are centrifuged and absorbed in a buffer containing 60% glycerol, 8% β-mercaptoethanol, 100 mM Tris pH 6.8, 0.1% SDS, 1% bromophenol blue, 1% xylene-cyanol blue. Total proteins are quantified by Bradford's method (BIO-RAD); equal quantities of proteins are then deposited on acrylamide gel without SDS (settlement gel: acrylamide 3.5%; bisacrylamide 0.12%; Tris-HCl 0.1 M pH 6.8/separation gel: acrylamide 10%; bisacrylamide 0.33%; Tris-HCl 0.4 M pH 8.8). Migration is effected at 13.5 mA in a buffer containing 25 mM Tris-OH, pH 8.8; 191 mM glycine for about 16 hours. The gel is then rinsed with water and equilibrated in the reaction buffer (67 mM Tris-maleate; 42 mM $MgCl_2$; 400 mM $NH_4Cl$; pH 7.1). Then a 1% agarose gel containing kanamycin sulphate (10.5 µg/ml) and 50 to 100 µCi $[\gamma\text{-}^{32}P]$ ATP is poured onto the gel of proteins. After reaction for 30 min, the phosphorylated kanamycin is transferred by capillarity on Whatman P81 ion exchanger paper. The P81 paper is then treated (1 mg/ml proteinase K, 1% SDS) to decrease the parasitic bands of phosphorylation of cell proteins, rinsed in phosphate buffer (10 mM $K_2PO_4$ pH 7.4) at 80° C., dried and autoradiographed.

B) RESULTS a) Obtaining and Sequencing of Mutants in the NTP-binding Motif of Protein C1.

The C1 protein of TYLCV contains the NTP-binding motif $GX_4GKT$ (residues 221 to 228).

Three mutations were introduced in the infectious clone pTYLCV to replace the $Lys^{227}$ (K) by three different amino acids: Ala (A), His (H) and Arg (R) (FIG. 3). The mutagenic oligonucleotides were designed in order to introduce, near the required mutation, a single restriction site for the enzyme PmlI (silent mutation), to facilitate selection of the clones exhibiting the mutation. In order to confirm the presence of the desired mutation and to be sure that no other mutation has been produced in this region, several independent clones were sequenced for each of the mutations (Ala, His and Arg).

b) Two of the Mutants Obtained are Deficient for their Replication.

Replication of the mutants was investigated by transfection of protoplasts obtained from a cell suspension of tobacco BY2. The various viral genomes, wild-type (pTYLCV) or mutated (pTYAla, pTYHis, pTYArg) were excised from their vector plasmid by enzyme Sst I, and are therefore transfected in linear double-stranded form. After culture for 3 and 5 days, appearance of the replicative forms of the virus is investigated by extraction of total nucleic acids, electrophoresis, transfer onto membrane and hybridization with a probe corresponding to the viral DNA. The results are shown in FIG. 4 for the infectious viral clone and the mutants pTYAla and pTYArg. The autoradiogram resulting from Southern analysis was quantified using an image analyser (Bio-Image, Millipore). The values shown on the graph correspond to the ratio of the optical density (OD) of the bands corresponding to the replicative forms, to the sum of the ODs of the bands corresponding to the transfected viral forms and to the replicative forms. In this way the percentage of replicative forms relative to the total viral forms is investigated.

FIG. 4 shows the percentage of replicative forms after three (in black) and five (in white) days of culture of the transfected cells. pTYLCV: wild-type viral genome; pTYAla, pTYArg: mutated viral genomes corresponding to change of K to A and R respectively.

It can be seen that the mutant pTYAla has a proportion of replicative forms much lower than that of the wild-type virus (by about a factor of 12). As for the mutant pTYArg, it shows a reduction by a factor of 3 relative to the wild-type. A similar effect was observed in another experiment. The experiments were not carried out with the mutant pTYHis.

Replication of the mutants pTYAla and pTYArg is altered, indicating that the potential NTP-binding site plays an important role in functioning of the C1 protein.

c) Investigation of a Trans-dominant Effect of the Mutated C1 Proteins on Replication by Means of Expression of the Reporter Gene NPT II:

The trans-dominant effect on the replication of viral DNA can be observed in two ways, either by accumulation of newly synthesized viral DNA, or by accumulation of a "reporter protein" coded by a recombinant virus. The reporter gene used here is the gene coding for neomycin phosphotransferase II (NPT II), introduced at the position of reading phases V1 and V2 of TYLCV. This modified viral genome (pTYneo) has the same replication capacities as an unmodified genome in isolated cells. The NPT II activity test is quantitative: the phosphorylated reaction product, and therefore the intensity of the autoradiography spot when using c-$^{32}$P ATP, is proportional to the amount of enzyme present (Reiss et al., 1984). Assuming that the intensity of NPT II activity increases with the number of viral genomes replicated, we investigated NPT II activity in the presence of the various constructs.

Figure 5:
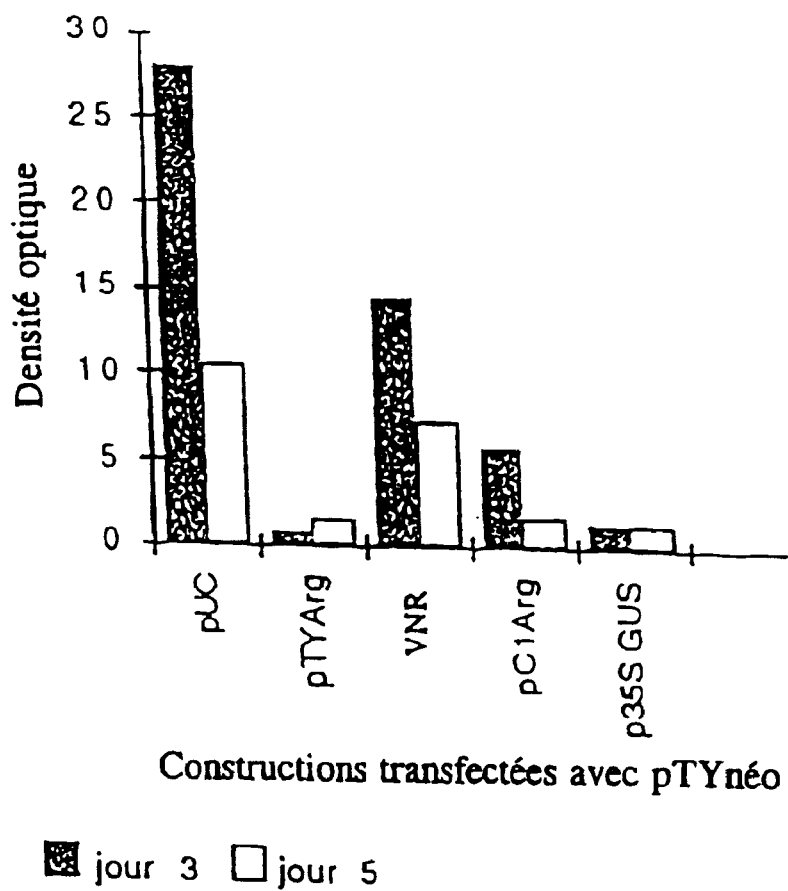
FIG. 5: graph representing the investigation of a transdominant effect of mutation K on R, NTP II activity test.

In order to investigate a trans-dominant effect, we cotransfected tobacco protoplasts on the one hand with the viral genomes, wild-type and mutated (pTYLCV, pTYAla, pTYHis, pTYArg), and on the other hand with the wild-type viral genomes and the expression cassettes of the mutated C1 ORFs (pC1Ala, pC1His, pC1Arg). We find a clear decrease of expression of the NPT II gene in the presence of the mutant virus pTYArg (by a factor of 37 at 3 days). Moreover, high-level expression of the mutated C1 protein (pC1 Arg) inhibits replication by a factor of 2.5 (FIG. 5).

However, we can see that in all cases the values of NPT II expression decrease between 3 and 5 days. As the structure bearing the NPT II gene is replicative, such a decrease of expression ought not to be observed. This kinetics suggests that the promoter of V1 and V2 is regulated as a function of the viral cycle. This method of detecting viral replication is therefore too indirect and is inappropriate, and will not be pursued for investigating the mutants pTYHis and pTYAla.

d) Mutated Viral Genomes in the NTP-binding Site Inhibit Replication of the Wild-type Genome.

This time, viral replication is investigated by quantifying the replicative viral forms accumulated in cells cotransfected with the viral genomes: wild-type (pTYLCV) and mutated (pTYAla, pTYHis, pTYArg). The methodology used is the same as for investigating the replication of the mutants. The presence of mutant viruses has an influence on replication of the wild-type virus (FIG. 6): thus, the mutants pTYAla and pTYArg decrease viral replication by a factor of 30 and 5.5 respectively. The effect is not very marked for the mutant pTYHis (factor of 1.4). These results are only the outcome of a single experiment, except for the mutant pTYArg, where the experiment was repeated and gave corroborating results.

We can see, with mutants pTYAla and pTYArg, that at 5 days the difference in the proportion of replicative forms between the wild-type virus and the mutants is less pronounced than at 3 days. This can be explained by a progressive accumulation of molecules evading inhibition, which therefore would not be complete in this system.

The mutants pTYAla and pTYArg therefore seem to inhibit replication of the wild-type virus. Nevertheless, it is difficult to attribute this inhibitory effect rigorously to the mutated C1 proteins. In fact, an effect of dilution of the functional C1 proteins must occur and interfere with the efficacy of replication. The C1 protein produced by the wild-type genome will in fact ensure replication of its own genome but also that of the mutant genomes, and so will be distributed over twice as many matrix molecules as in the control used here (pUC 118) where the wild-type viral genome is cotransfected with a plasmid to which C1 does not bind. It will be interesting to perform an additional check, in which a wild-type virus is cotransfected with a mutated virus that does not produce any C1 protein (by deletion of the ORF C1 or by introduction of a stop codon). If there is also a decrease of viral replication, it is then a question of a titration effect of the C1 proteins and not a dominant negative effect.

e) Overexpressed Mutated C1 Proteins have a Dominant Negative Effect: they are Capable of Inhibiting in trans the Replication of the Wild-type Viral Genome.

In order to see whether the mutated C1 proteins in the NTP-binding site, expressed at high level, can inhibit the replication of the wild-type viral genome, the corresponding ORFs were put under the control of a strong promoter (pC1Ala, pC1His, pC1Arg). The constructs thus obtained were tested for their effect on replication by cotransfection of protoplasts with a wild-type viral genome.

The pC1Ala and pC1His plasmids exert pronounced inhibition of replication of the wild-type virus (decrease by a factor of 38.5 and 14.5 respectively, relative to the reference used). Other experiments have shown a change in the same direction, but this time pC1His has a stronger effect than pC1Ala. As for the pC1Arg plasmid, its effect is not significant, as the reduction factor is only 1.4. This tends to support the hypothesis of dilution of molecules in the case of cotransfection of intact viral genomes. In fact, with this same mutation, we were able to see an effect of decrease of viral replication which, curiously, is not found in the case of overexpression.

Figure 7:
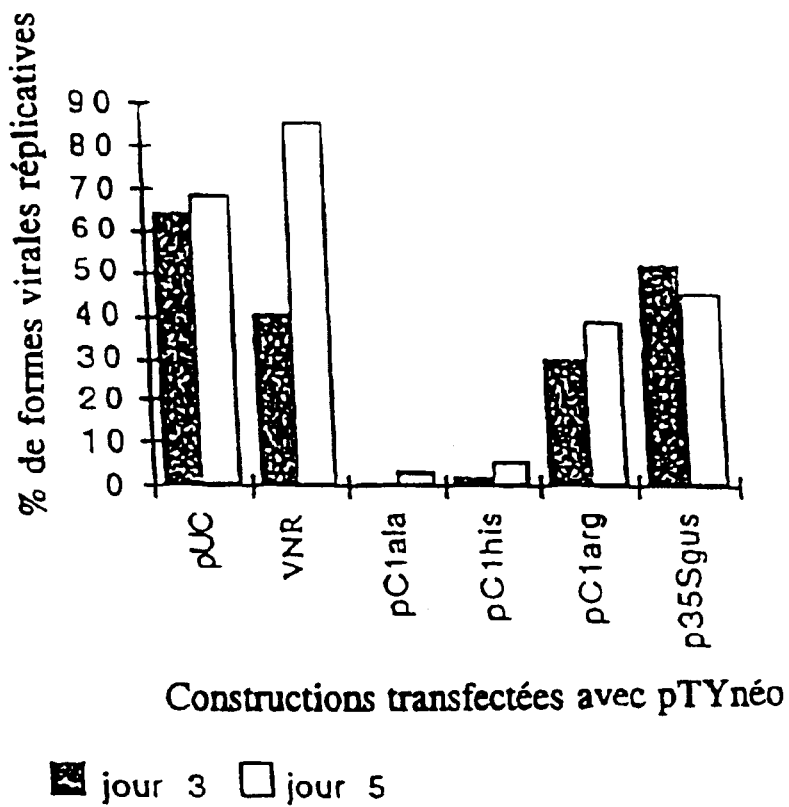
FIG. 7: graph representing the effect of cotransfection of constructs permitting the high-level expression of mutated C1 proteins (pC1Ala, pC1His, pC1Arg) on the replication of the wild-type virus (pTYNeo)

A cotransfection control was conducted with pTYneo and an expression cassette of the protein GUS (β-glucuronidase), the promoter then used being the 35S promoter of the CaMV. This transfection was performed with the aim of evaluating the consequences of overexpression of any protein. In the two experiments that were performed, the results were contradictory, for in one case the effect seems to be zero, whereas in the other case it caused a decrease of the replicative forms by a factor of 4 (FIG. 5 and FIG. 7).

Conclusion

Alteration of the potential NTP-binding site of the C1 protein of TYLCV results in obtaining viral genomes that are deficient for their replication. This demonstrates the importance of this site in the function of the C1 protein and strongly suggests that the C1 protein is undoubtedly capable of binding to an NTP. Moreover, the mutated viral genomes (pTYAla and pTYArg) can retard the replication of their wild-type homologue. A similar effect has been demonstrated with an expression vector of the mutated C1 proteins, for the Ala and His mutations.

It therefore seems that the negative phenotype of the mutated C1 proteins is effectively dominant over their wild-type homologue, and so leads to inhibition of viral replication. In fact the inhibition of replication observed in the case of cotransfection of intact viral genomes cannot be explained solely by an effect of dilution of the wild-type C1 proteins, since the mutant pTYHis does not induce a very great change. However, the effect of overexpression of an exogenous protein (GUS) remains to be defined.

Various mechanisms can account for a dominant negative effect of the mutated C1 proteins. It is possible that the C1 protein is multimeric and that the mutated subunits combine with their wild-type homologue, rendering heterologous multimers non-functional. Another possibility is that the mutated C1 proteins compete with the wild-type proteins for a limiting substrate. This substrate might be a cell protein, or the viral DNA itself. The hypothetical complex thus formed would be transient and productive when it contains the wild-type C1 protein, but incapable of evolving further if there is no binding to NTPs or hydrolysis of the latter.

It is surprising that dominant negative phenotypes are obtained in the case of cotransfection of viral genomes. In fact it is difficult to imagine such a radical effect of inhibition with unmutated and mutated C1 proteins expressed at an identical level. There might be spontaneous overexpression of the mutated C1 proteins, which can occur if the C1 protein controls its own expression. Thus, it is conceivable that the C1 protein interacts normally with a cellular cofactor to perform negative retro-control on its production, it has been seen, furthermore, that the transcripts of C1 are present in small quantity relative to the transcripts coded by the viral strand. The mutated C1 proteins have perhaps lost this ability to interact with a cofactor to form a negative control complex. This would then lead to overexpression of the mutated proteins, which are gradually amplified and then acquire the ability to inhibit the wild-type proteins, as is the case for the Rep proteins of the Adeno Associated Virus (AAV) (Chejanovsky and Carter, 1990).

II) DEMONSTRATION OF ATPase ACTIVITY IN VITRO FOR THE C1 PROTEIN OF A GEMINIVIRUS, STYLCV. INVESTIGATION OF MUTATIONS IN ITS NTP-BINDING SITE

A) MATERIAL AND METHODS

Several classical techniques of molecular biology were employed following the protocols indicated by Sambrook et al. (1989), Ausubel et al. (1989), or by the suppliers; they will not be described in detail here.

1. Biochemical Investigation of ATPase Activity in vitro of the Wild-type or Mutated C1 Protein 1.1. Production of Wild-type or Mutated C1 Protein A "wild-type" GST-C1 fusion protein was obtained. The construct expressed in *E. coil* is placed in the plasmid pGEX3(Amrad), under the control of an IPTG-inducible lac promoter (see FIG. 8).

To obtain the same construct with the various mutations investigated, the 500 bp SalI-SstI fragment of the pGEX-C1 plasmid is replaced by the corresponding fragment of the plasmids pTY-Ala, Arg, His and Pml (FIG. 8). Production of these plasmids is described in paragraph 2 below.

The pGEX-C1 vector, as well as the various inserts, are purified after digestion by the enzymes SalI and SstI on low melting-point 1% agarose gel. Ligation is performed by means of ligase T4 (ligase: 400 units; vector: 50 ng; insert: 150 ng) over night at 16° C. The *E. coli* strain DH5α is transformed with the constructs obtained, then the bacterial DNA is extracted by alkaline lysis. The constructs are digested by the enzyme PmlI, in order to demonstrate the existence of the corresponding site in the mutants.

After culture of the bacteria in the presence of the inducer (IPTG 0.2 mM), the proteins are extracted by treatment with ultrasound (sonication) (VibraCell 3×30", setting 4.5). The proteins containing a functional GST part are retained on agarose-glutathione beads, washed with MTPBS# buffer (#: see appendix) to eliminate the contaminating bacterial proteins, then eluted in a solution of glutathione 5 mM, Tris pH8 15 mM.

The presence of the wild-type or mutated GST-C1 protein is monitored before and after purification by depositing an aliquot on Laemmli 10%# denaturing gel and staining with Coomassie blue#.

1.2. Investigation of ATPase Activity in vitro of the Wild-type or Mutated C1 Protein (according to Traut, 1990)

Mix 20 ml of ATPase(×2) buffer (composition: see below) with 20 ml of purified protein fraction (about 50 ng). Leave the mixture to incubate at 25° C. Stop the reaction after the desired time by adding 200 ml of activated carbon (7.5% of activated carbon in 50 mM HCl, 5 mM $H_3PO_4$).

The activated carbon binds the ATP, but not the inorganic phosphate liberated by any ATPase activity.

The carbon is then removed by centrifugation (5 min at 13000 rpm in an Eppendorf tube). The radioactivity of the supernatant is measured using a scintillation counter (Beckman LS 7500) after adding 4 ml of scintillation liquid.

ATPase ×2 buffer: Pipes/NaOH pH 7.0 50 mM; NaCl 200 mM;

$MgCl_2$ 10 mM; NP40 0.02%; ATP 10 mM.

Add 0.37 MBq (10 mCi) of γ-$^{32}$P-ATP to 400 μl of this solution before use.

2. Directed Mutagenesis 2.1. Choice of Mutants

The manner of obtaining the plasmids pTYAla, pTYHis and pTYArg is described in paragraph I)A)a) above. Two other mutants were obtained:

- a "nonsense" mutant in which an Ochre codon (TAA) is introduced 30 nucleotides downstream from the initiation codon of ORF C1. With this mutant it is possible to study the effect of the RNA of C1 alone, without production of the corresponding protein. It is called Stop mutant.
- a mutant Pml, in which only the site PmlI, created in the mutants Ala, Arg and His to facilitate their selection, is introduced. This construct makes it possible to confirm the absence of an effect of this silent mutation for the C1 protein.

2.2. Production of the Pml and Stop Mutants

The principle of the method employed was described by Kunkel in 1985: the required mutation is obtained by hybridization of a mutagenic oligonucleotide with the single-stranded viral DNA then synthesis of the complementary strand in vitro. The unmutated DNA is then counter-selected (as described above).

Two mutagenic oligonucleotides were used:

"Stop" oligonucleotide:

5' GTATCAAGGCT(AGATCT)TAATTCCTTACATATCCC 3' (SEQ ID NO:16)

"Pml" oligonucleotide:

5' CCGGACAGGAAAGAC(CACGTG)GGCC 3' (SEQ ID NO:17)

The new restriction site created during mutagenesis (BglII for the "Stop" mutant, PmlI for the "Pml" mutant) is shown in parentheses. The nonsense codon Ochre (TAA) introduced is underlined.

2.3. Sequencing of the Mutants Obtained

The mutants were sequenced by means of the Pharmacia kit (Sequenase), which uses the method of chain termination of Sanger et al. (1977).

The reactions obtained are deposited on 6% acrylamide denaturing gel with constant thickness of 0.4 mm. Migration is performed in TBE buffer (Sambrook et al., 1989) at 60 W. The DNA, labelled with α$^{33}$P-dCTP or α$^{35}$S-dCTP, is revealed by autoradiography.

3. Investigation of the Replication of Viral DNA in Tobacco Protoplasts (As described above)

3.1. Production of the Protoplasts (As described above)

3.2. Transfection of the Protoplasts and Southern Blot (As described above)

4. Production of Transgenic Plants Possessing a Gene that Codes for the Wild-type or Mutated C1 Protein 4.1. Constructs Introduced The intact ORF C1, wild-type or mutated, is cloned in the binary vector pGA492 (An et al., 1987), downstream of the 35S promoter of the cauliflower mosaic virus, which permits constitutive expression of the ORF C1 in the transformed plants. The construct employed is shown in detail in FIG. 9.

The $^{35}$S-C1 construct as well as the NPTII gene conferring resistance to kanamycin, located between the borders of the T-DNA of *Agrobacterium tumefaciens*, are transferred into the genome of the plant cells, where they are integrated in an uncontrolled manner (as to position and number of copies).

Figure 10:
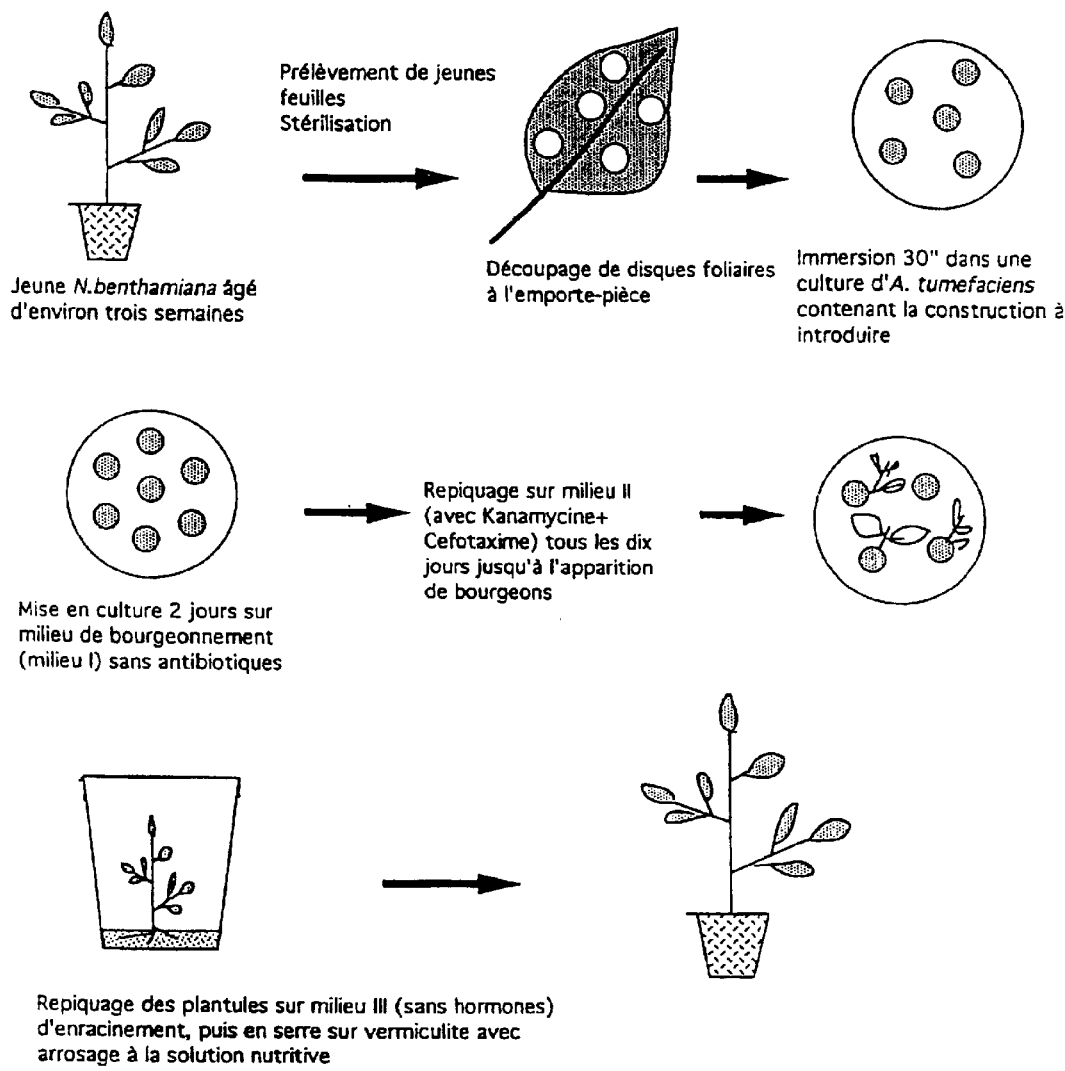
FIG. 10: transformation of leaf discs of *N. benthamiana* and obtaining transgenic plants expressing the wild-type or mutated ORF C1.

4.2. Transformation of Leaf Discs of *Nicotiana benthamiana* and Production of Transgenic Plants FIG. 10 shows the protocol followed for transformation of *N. benthamiana* by *A. tumefaciens* and regeneration of transgenic plants. Plantlets can be acclimatized in the greenhouse about two months after transformation of the leaf discs.

4.3. Control of Expression of the ORF C1 in the Plants Obtained

The plants obtained were kept, throughout their period of culture in vitro, on a selective medium (kanamycin 70 mg/l), which makes it possible in principle to preserve only those that have integrated the required construct.

However, certain checks have to be done to be sure of this.

An "NPTII test" as described above was carried out starting from extract from regenerated plants, acclimatized in the greenhouse.

B) RESULTS

1. ATPase Activity in vitro of the Wild-type or Mutated C1 Protein 1.1. ATPase Activity of the Wild-type C1 Protein The C1 protein used is a GST-C1 fusion protein.

The method used for measuring the ATPase activity of the C1 protein makes it possible to demonstrate the liberation of inorganic phosphate from ATP. In the case of the wild-type GST-C1 protein, various experiments have demonstrated the existence of such activity: from 20 to 40% of the total radioactivity introduced is released in the supernatant at the end of the reaction previously described, which indicates hydrolysis of a percentage close to that of the ATP introduced. In control tests with GST alone, or with the enzyme buffer, just 2 to 4% of the radioactivity introduced is found in the supernatant in parallel experiments conducted in the same conditions.

These results appear to indicate an ATPase activity of the C1 protein itself The technique employed does not make it possible to determine whether the activity of the C1 protein leads to the production of ADP or AMP. The maximum percentage of ATP hydrolysed may be related either to a concentration of released product inhibiting the function of the enzyme, or to degradation of the latter after 15 to 30 min of reaction. To determine the cause of this limit, experiments with variation of the concentration of the enzyme or of ATP have to be carried out. It also remains to determine whether the C1 protein is capable of hydrolysing other nucleotides, in particular GTP.

If the ATPase activity detected is effectively that of C1, and not of a contaminant of bacterial origin, the C1 protein must bind ATP. The NTP-binding site therefore seems functional, which means we can assume that mutations at this site can be the cause of dominant negative phenotypes, as is the case in other models (Chejanovsky and Carter, 1990; Han and Sternberg 1991).

The mutated proteins Ala, Arg, His and Pml were therefore constructed, expressed in *E. coli* and purified.

1.2. Production and ATPase Activity of Mutated C1 Proteins

* Production of C1 Proteins Carrying Ala, Arg, His and Pml Mutations

Proteins bearing the Ala, Arg, His and Pml mutations were obtained using the protocol described above.

The GST or GST-C1 proteins obtained are extracted from bacteria and purified on agarose-glutathione beads. In contrast to the case of GST alone, the quantity of GST-C1 proteins obtained after purification is small, and contaminants are still numerous. Nevertheless, the degree of purity and the protein concentration seem comparable for the wild-type and mutated C1 proteins. The mutated proteins do not seem to be affected in their stability relative to the wild-type C1 protein.

* ATPase Activity of the Mutated C1 Proteins Alone

The ATPase activity of the mutated proteins is measured according to the protocol used for the wild-type C1 protein. The ATPase activity of the Ala and His mutants is comparable to that of the GST alone, and so can be likened to a "background noise". The Arg mutant possesses an activity which reaches nearly half that of the wild-type C1 protein. The Pml mutant, which can be likened to the wild-type protein since the mutation introduced is silent, effectively possesses an ATPase activity comparable to that of the wild-type protein.

The decrease in ATPase activity in the Arg mutant and its complete loss in the Ala and His mutants show the importance of a point mutation at the site presumed to be the NTP-binding site of the C1 protein of TYLCV. This site therefore seems to be functional in the C1 protein, and lysine plays a key role in its functioning.

Limited purification of the C1 protein allows us to envisage the possibility of ATPase activity linked to the presence of bacterial contaminants. Nevertheless, it seems unlikely that these possible contaminants are eliminated in a specific manner in the mutated proteins.

For the hypothesis of activity linked to bacterial contaminants to be eliminated completely, the method envisaged is labelling of ATPase with $\gamma^{35}$S-ATP, which is capable of binding to the enzymes but not of being hydrolysed. After migration on gel and autoradiography, labelling ought to appear for a protein of the size of the GST-C1 fusion (65 kDa), then after cleavage of the fusion protein by an enterokinase, for a protein that has the apparent molecular weight of the C1 protein (42 kDa).

This technique should also make it possible to determine whether the mutants that have lost their ATPase activity are still capable of binding ATP, as is the case for the RAD3 protein of yeast (Sung et al., 1988).

* ATPase Activity of Wild-type and Mutated C1 Proteins

The ATPase activity of a mixture of wild-type and mutated C1 proteins was investigated. The wild-type C1 and GST mixture is regarded as a reference, as no dominant negative effect of GST is expected.

The mutated proteins do not seem to have any effect on the function of the wild-type protein, the total activity obtained being almost equal to the sum of the activities of each of the components of the mixture.

The results obtained with the wild-type and mutated C1 proteins seem to indicate ATPase activity of the wild-type C1 protein, relative to the binding of ATP at the site defined by Walker (1982).

Hydrolysis of the ATP probably supplies the energy necessary for another activity of C1, which remains to be determined.

ATPase activity does not seem to be linked to the cleavage of single-stranded DNA, as the latter does not require supply of ATP. Moreover, proteins that had lost their capacity for cleavage on account of a mutation located in a domain presumed to be independent of the NTP-binding site maintained their ATPase activity.

III) RESISTANCE DERIVED FROM THE PATHOGEN: A PROTECTED DOMINANT NEGATIVE PROTEIN OF PLANTS OF *NICOTIANA BENTHAMIANA* AGAINST THE STYLC VIRUS

A) MATERIAL AND METHODS

1. INVESTIGATION OF REPLICATION OF VIRAL DNA IN PROTOPLASTS a. Transfection of Tomato Protoplasts A cell suspension of the interspecific hybrid *Lycopersicon esculentum×L. pennellii* is cultivated for four days in MSI* medium (*: see appendix below) at 25° C. and with stirring at 100 rpm. The cells are collected by centrifugation (200 g, 5 min) and washed twice with CPW* medium. The cell walls are then digested with three volumes of enzyme solution* for 3 hours with stirring, at 25° C. and in the dark.

The protoplasts thus obtained are then filtered twice on sieves of 300 μm then 140 μm, collected by centrifugation (90 g, 5 min) and washed twice with TM2* medium. The protoplasts are counted in a Fuchs-Rosenthal cell and absorbed to a concentration of $10^6$ protoplasts/ml.

Then 50 μg of calf thymus DNA, 10 μg of SstI-linearized double-stranded viral DNA and 0.5 ml of PEG 1500 solution (40% in medium F*) are added to $5 \times 10^5$ protoplasts. The suspension of protoplasts is then diluted at intervals of 10 min with medium F* (final volume 10 ml). The protoplasts are collected (90 g, 5 min) and cultivated at a concentration of $10^5$/ml in medium TM2* in diffuse light at 25° C. The cells are collected seven days later for extraction of the total DNA.

1b. Extraction of Total DNA from Transfected Protoplasts
(As described above)

1c. Southern Blot Analysis of the DNA
(As described above)

2. INVESTIGATION OF STYLCV-RESISTANT TRANSGENIC PLANTS

2a. Agroinoculation of Transgenic Plants (primary regenerants)

Transgenic plants of *N. benthamiana* (Ala, His, Arg and Stop) were obtained by transformation with various mutated C1 genes (Ala, His, Arg and Stop) (Desbiez, DEA 1993). The lineage obtained after self-fertilization (F1) of the first regenerants (R) was sown without selection and the plants obtained (F1) were tested for their sensitivity or resistance to the wild-type STYLCV; see FIG. 11.

Since STYLCV cannot be transmitted mechanically, the technique of agroinoculation or agroinfection (Grimsley et al., 1986) was used for infecting transgenic F1 plants of *N. benthamiana*. This technique makes it possible to introduce the viral genome into the plants by means of the T-DNA of *Agrobacterium tumefaciens*.

The wild-type STYLCV was cloned in the form of 1.8 mer in the binary vector pBin19, thus becoming the plasmid pBIN19/TYLCV-S 1.8 mer (Kheyr-Pour et al., 1991). The transformed bacteria were selected on solid YEB* medium with addition of kanamycin (100 μg/ml), rifampicin (150 μg/ml) and neomycin (20 μg/ml). The *A. tumefaciens* LBA4404/pBin19/TYLCV-S 1.8 mer was cultivated in 20 ml of liquid YEB* (with antibiotics added as stated above), at 28° C. with stirring (200 rpm) and in the dark. After incubation for 48 h, the bacteria were washed twice with sterile water then resuspended in 10 ml of sterile water.

For agroinoculation, plants with age of about three to four weeks were used. The suspension of *A. tumefaciens* LBA4404/pBin19/TYLCV-S 1.8 mer is injected using a 1 ml syringe at the level of the leafstalks of three young leaves.

The plants are placed in chambers at 24° C., photoperiod of 16 h and 70% humidity (with disinfection of the drainage water, to avoid contamination of the environment).

Twenty-five plants are agroinoculated for each experiment. Two transgenic plants and two normal plants of *N. benthamiana* are inoculated with sterile water (negative control). Another two normal plants of *N. benthamiana* are inoculated in the same conditions with the strain of *A. tumefaciens* described above (positive control). The plants are monitored regularly to observe the appearance of symptoms. One month after agroinoculation, the first characteristic symptoms (leaf roll and yellowing) appear in the non-transgenic control plants.

2b. Detection of the Different Forms of Viral DNA

The presence of single-stranded viral DNA in the agroinoculated plants is detected by the "foliar squash" method (Navot et al., 1989): a young leaf is squashed on a nylon membrane, and its DNA is fixed with UV. Without prior denaturation, the membrane is hybridized with a probe corresponding to the total STYLCV DNA labelled with [Ó-$^{32}$P] dCTP.

To confirm the presence of other forms of viral DNA, a Southern blot is performed. The total DNA is extracted by the technique of Matzeit et al. (1991), followed by a series of phenolic extractions, and finally the DNA is precipitated with ethanol. 5 μg of DNA is deposited in a 1% agarose gel (TAE×1*) at 2 V/cm and analysed by Southern blot (see above § 1.c).

2c. Agroinoculation of Leaf Discs

A culture of *A. tumefaciens* LBA4404/pBin19/TYLCV-S 1.8 mer is maintained for 48 h (see above, agroinoculation of transgenic plants). The agrobacteria are washed and resuspended in medium MS 30*. For each plant, two young leaves are decontaminated with sodium dichloroisocyanurate (Bayrochlor, 1 tablet per liter) for 15 min. Leaf discs are cut out and immersed for 1 min in the suspension of agrobacteria. The discs are then dried on sterile paper, and then deposited on medium A*. After 48 h, the discs are transferred to medium B*. The total DNA is extracted seven days after agroinoculation (see below).

2d. Extraction of Total DNA from Transgenic Plants or from Leaf Discs Agroinoculated with STYLCV A gram of young leaves (or of leaf discs) is pulverized in liquid nitrogen and resuspended in 5 ml of TNES* solution. Two phenolic extractions are carried out to remove the cell debris and the proteins. The nucleic acids (DNA and RNA) are precipitated in the presence of 0.3 M sodium acetate (pH 5.2) and 70% ethanol (final %), dried and absorbed in 200 μl of sterile TE (Tris 10 mM, EDTA 1 mM). The RNAs are removed by treatment with RNase A (final concentration 200 μg/ml) for 1 h at 37° C. The optical density at 260 nm is measured. 5 μg of DNA is deposited in a gel of 1% agarose in TAE×1 (migration 2 V/cm, 15 h) and analysed by Southern blot.

3. DETERMINATION OF THE NUMBER OF INSERTS IN F1 ALA1 PLANTS

3a. Segregation in vitro on Kanamycin

To determine the concentration of kanamycin necessary for arresting plant growth, a range of concentrations was used for nontransformed *N. benthamiana* (70, 100, 150, 200 and 300 μg/ml). The F1 seeds are sown on MS30* medium, which contains kanamycin at 150 μg/ml, and were observed regularly for discoloration of the leaves.

3b. Southern Blot

5 μg of genomic DNA extracted from leaves of transgenic F1 Ala1 plants before agroinoculation are digested by HindIII (this enzyme is chosen because it cuts just once at the level of the 35S-C1 insert). The digested DNA fragments are separated in gel of 1% agarose in TAE×1* (5 V/cm for 5 h), then transferred onto a membrane of nylon Hybond-N (Amersham) for 6 h by capillarity with SSC×20*. The membrane is then hybridized with a DNA C1 PflMI-BglII probe (obtained by cutting, with PflMI and BglII, viral DNA cloned in pUC118 at the level of site SstI and separation in low-melting-point agarose gel) labelled by random priming with [α-$^{32}$P] dCTP and treated in the same way as above (see Southern analysis of DNA, P21 1.c).

4. ANALYSIS OF PROTEINS BY WESTERN BLOT

4a. Extraction of Total Proteins from Plants 500 mg of young leaves are pulverized in liquid nitrogen, and the total proteins are precipitated with trichloroacetic acid 10% (4 ml/g). The deposit is washed once with 100% acetone then three times with 90% acetone, before being dried for the whole night with the Speed-Vac (Savant). The deposit is absorbed in 400 μl of Tris-Glycine buffer (25 mM Tris, 250 mM glycine). The concentration of total proteins is determined at 280 nm. To 20 μl of the supernatant (containing 50 μg of total proteins), add 4 μl of 6×SDS* buffer and heat the whole to 100° C. for 4 min and immediately load onto polyacrylamide gel (12.5%) in the presence of 0.1% SDS. Migration is performed for 1 h at 20 V/cm. The gel is then transferred onto nylon Hybond-C extra membrane (Amersham), in the presence of Tris-Glycine buffer, for 16 h at 2 V/cm.

4b. Preadsorption of the Anti-C1 Antibody with Protein Extract of Non-transgenic *N. benthamiana*

The anti-C1 polyclonal antibody was prepared in the laboratory by purifying, on polyacrylamide gel, the band corresponding to the fusion protein GST-C1 (produced in *E. coli*) and inoculation in a rabbit. 10 μl of anti-C1 polyclonal antibodies are incubated with 50 μl of total protein extract from non-transgenic *N. benthamiana* for the whole night at room temperature. The solution is then centrifuged at 17000 g for 5 min, at room temperature, and the supernatant is recovered.

4c. Incubation of the Membrane with Preadsorbed Anti-C1 Antibody

The membrane is incubated for one hour with a solution of PBS*, Tween20 0.1%, skimmed milk Gloria 5% (to saturate the non-specific sites of fixation of the membrane to the antibody). The previously preadsorbed anti-C1 antibodies are added to the membrane for 2 h at room temperature (dilution 1/10000). Then three washings are effected in PBS, Tween20 0.1%. The membrane is then incubated in goat serum anti-IgG-rabbit conjugated with alkaline phosphatase (Sigma) (dilution 1/9500) for 2 h at room temperature. The membrane is then washed in PBS, Tween20 0.1%. The antigen-antibody complex is developed in 15 ml of substrate* buffer in the presence of 100 μl of Nitro Blue Tetrazolium (NBT: stock solution at 50 mg/ml, Sigma) and 50 μl of 5-bromo-4-chloro-3-indoyl phosphate (BCIP: stock solution at 50 mg/ml, Sigma). A brown precipitate appears and the reaction is stopped in doubly-distilled water, the whole at room temperature and in the light.

B) RESULTS a) REPLICATION OF WILD-TYPE AND MUTATED VIRAL GENOMES IN TOMATO PROTOPLASTS

To examine for a possible dominant negative effect in vivo of the C1 protein mutated at the level of the P-loop on the replication of wild-type viral DNA, the viral genomes (wild-type and mutated) are cotransfected in tomato protoplasts. The benefit of such a system is that it makes it possible to investigate the replication of viral DNA independently of the phenomena of systemic movement of the virus.

The plasmid pTY contains the intact wild-type viral double-stranded genome of the STYLCV cloned at site SstI of the pUC118 vector. The plasmids pTYAla, pTYHis and pTYArg are identical to pTY, except that they have a point mutation replacing the Lys$^{227}$ by alanine, histidine and arginine, respectively. The plasmid pTYStop contains a nonsense mutation 30 nt downstream from the initiation codon of translation of ORF C1. Owing to the cell ligases, the monomers of viral genomes introduced, linearized by SstI, are recircularized and thus serve as intermediate replicative forms in the viral cycle.

Figure 11:
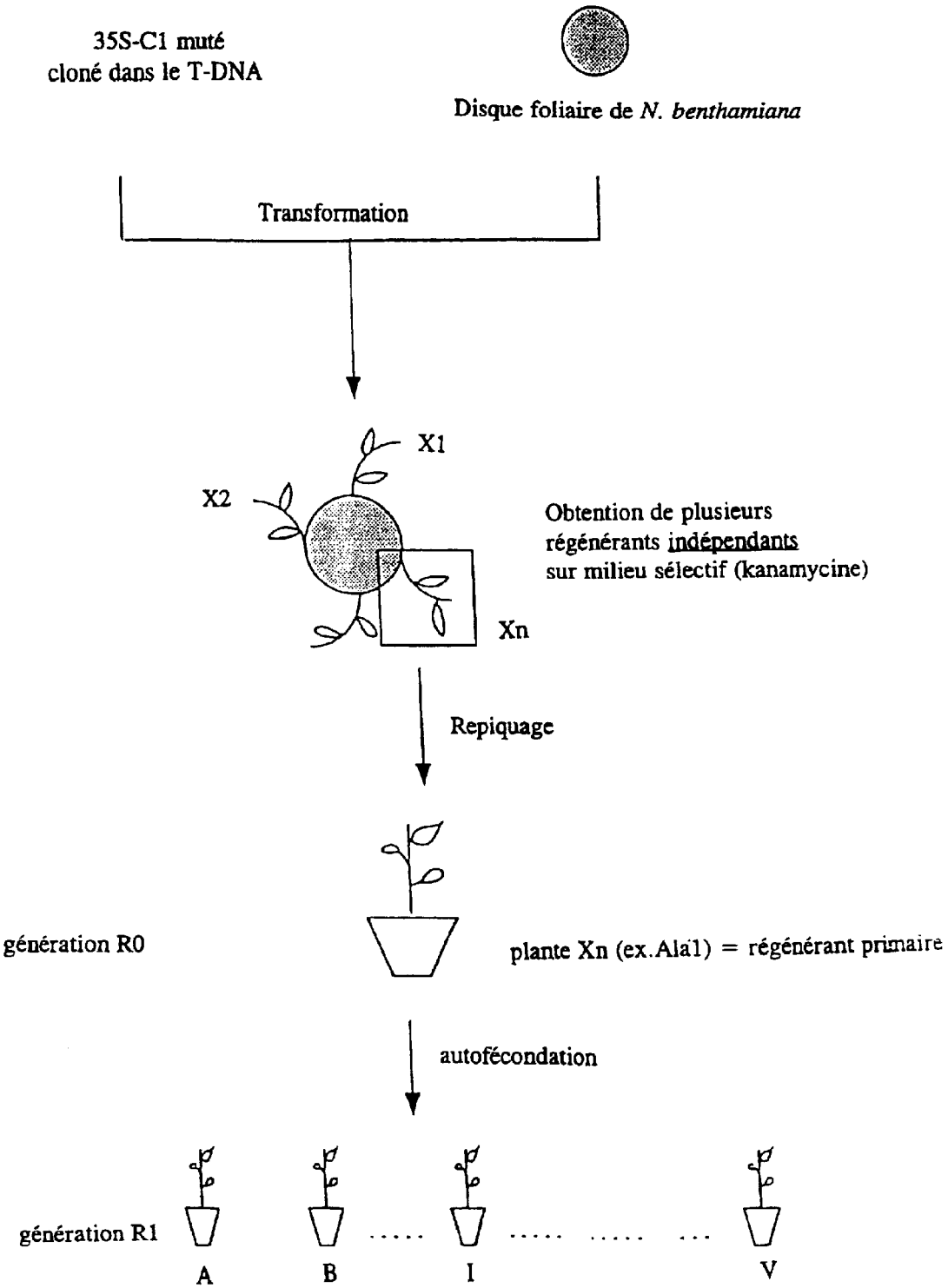
FIG. 11: simplified diagram explaining the obtaining of plants of the first generation F1.

When tomato protoplasts are transfected with the wild-type viral DNA alone, the various forms of single-stranded (ss) and supercoiled double-stranded (ds) viral DNA accumulate and are detected. This is evidence of de novo replication of the wild-type viral genome in the protoplasts (see FIG. 12). The mutant pTYStop, as expected, does not replicate (as there is no translation of the RNA). The mutant pTYArg replicates, but not so well as the wild-type. On the other hand the mutants pTYAla and pTYHis (which are deficient in ATPase activity in vitro) do not replicate (or replicate at a level that cannot be detected) (FIG. 11). These results suggest that the P-loop (and probably ATPase activity) is necessary for replication of the viral DNA and confirm the results presented in the aforementioned FIG. 4.

Figure 12:
FIG. 12: replication of the DNA of STYLCV in tomato protoplasts.

When the wild-type viral DNA is cotransfected with the mutated viral DNAs, interesting results are obtained. In the presence of pTYArg or pTYHis, replication of the wild-type viral DNA is apparently unaltered (presence of the ss and ds forms). In contrast, pTYAla has a considerable effect on the replication of the wild-type viral DNA, since the ss form is absent (or undetectable) and the ds form is present in a smaller amount (FIG. 12). This ds form is probably generated by circularization of the linear viral DNA introduced owing to the cell ligases. These results clearly show a dominant negative effect of the mutated viral genome pTYAla on replication of the wild-type viral DNA, which confirms the results presented in the aforementioned FIG. 6.

b) AGROINOCULATION OF F1 PLANTS BY THE WILD-TYPE STYLCV

In order to see whether the plants transformed by the various mutated C1 genes are resistant to the wild-type STYLCV, agroinoculation experiments are conducted (Grimsley et al., 1986). Plants of *N. benthamiana* were transformed by the various mutated C1 genes (C1-Ala, C1-His, C1-Arg and C1-Stop) placed under the control of the 35S promoter of the cauliflower mosaic virus (CaMV). The corresponding regenerants were obtained respectively (Ala, His, Arg and Stop) (Desbiez, DEA 1993). The first filial generation F1 of these plants, obtained by self-fertilization, is sown and the plants at age of about one month are agroinoculated with the STYLCV. Following agroinoculation, virus monomers are liberated from the 1.8-mer probably by homologous recombination. The liberated viral monomers replicate and infect the plant systemically. Three to four weeks after agroinoculation, the first symptoms (leaf curl) appear. Presence of the viral ss DNA is detected by the leaf squash technique (Navot et al., 1989), and is confirmed by analysis of the total DNA of these plants by Southern blot.

The non-transgenic *N. benthamiana* plants (positive control) are diseased and, in leaf squash, give a strong signal of hybridization with a total DNA probe of STYLCV. All the Arg1, His21 and Stop6 plants are diseased and they all give a strong signal of hybridization with the same probe. In contrast, out of 14 Ala1 plants agroinoculated in the same conditions, seven exhibit neither symptoms nor hybridization with the probe. Analysis of total DNA by Southern blot shows for these plants a total absence of the various forms of viral DNA, whereas the sensitive plants certainly do have the various forms of viral DNA (ss, ds and relaxed circular form (oc)).

To confirm these results, leaf discs of potentially resistant plants are agroinoculated with the STYLCV. Seven days after agroinoculation, the various forms of viral DNA (ss and ds) are detected in the leaf discs of non-transgenic *N. benthamiana*. This provides evidence of good infectivity of the clone used for inoculating the leaf discs. Three plants display very reduced replication relative to a positive control: these are resistant plants (absence of symptoms, but residual replication of the viral DNA). Two plants do not have any form of viral DNA: these are completely resistant plants. Curiously, two plants have the various forms of viral DNA, whereas no signal was visible in squash or in Southern blot. This might be explained by the "inoculum pressure" used in the experiments of agroinoculation of leaf discs. This "inoculum pressure" is higher than was used in the agroinoculation of whole plants, and so would lead to a change of the ratio of mutated to wild-type C1 proteins in favour of the wild-type protein, and consequently to replication of the viral DNA. On the other hand this (ambiguous) behaviour might correspond to an inhibition of the movement (at long range?) of the virus in planta, since the agroinoculation of leaf discs makes it possible to avoid phenomena of movement at long range.

Furthermore, three other F1 filial generations of Ala plants that came from separate regenerants (Ala14, Ala30 and Ala44) are available. The agroinoculation of thirty-five F1 Ala30 plants with the STYLCV revealed the existence of 29 potentially resistant plants. This result reinforces that obtained with the F1 generation of Ala1.

c) MOLECULAR CHARACTERIZATION OF ALA1 PLANTS RESISTANT TO TYLCV

The presence and number of copies of the C1-Ala gene that are present in the genome of the Ala1 plants is determined by two complementary approaches. The first, genetic, is based on investigation of segregation of the kanamycin-resistance phenotype ($kan^R$). This phenotype is conferred by the neomycin phosphotransferase gene (NPTII of transposon Tn5) introduced with the mutated C1 gene to facilitate selection of the transformants. The second, molecular, consists of digesting the genomic DNA and conducting a Southern analysis.

Expression of the C1-Ala gene is analysed at the protein level by Western blot.

1. Determination of the Number of Copies of the C1-Ala Gene

* Genetic Approach

A range of concentration of kanamycin is effected for *N. benthamiana* in order to determine the concentration that is necessary for arresting plant growth (discoloration of the leaves). The results showed that to obtain visible effects it was necessary to use a kanamycin concentration above 100 mg/l. Therefore a concentration of 150 mg/l is used.

A segregation of the type 3 $kan^R$:1 $kan^S$ would correspond theoretically to the insertion of a single copy of T-DNA in the plant genome, whereas a segregation of type 15 $kan^R$:1 $kan^S$ would correspond to the insertion of two copies of T-DNA.

Of 89 Ala1 plants sown, 7 are $kan^S$ and 82 are $kan^R$. The $\chi^2$ test shows that these values are in keeping with a segregation of type 15:1 ($\chi^2$=0.45 and a<0.001, therefore the difference is not significant and there is less than one chance in a thousand that our hypothesis is not valid). These results suggest that the primary regenerant Ala1 contained at least two copies of T-DNA of which the NPTII genes are expressed.

This method can nevertheless be criticized on two counts:
The $kan^R$ phenotype is conferred by the NPTII gene, and it could be that a modification or a loss of this gene occurred: we would then have a $kan^S$ phenotype even though the C1 gene is present. The opposite situation might equally occur, with loss of the C1 gene and presence of the NPTII gene ($kan^R$).

If the plant contains more than two copies of the C1 gene, the results of segregation become difficult to interpret. It is necessary either to increase the sample size, or investigate the $kan^R/kan^S$ segregation of the F2 filial generation.

* Molecular Approach

In order to determine the exact number of copies of the C1-Ala gene that are present in the Ala1 transformed plants, the DNA of these plants is digested with HindIII. As this enzyme only cuts once at the level of the C1 gene, the number of bands that will be revealed corresponds to the number of C1-Ala inserts. The minimum size expected is 1530 bp. For complete enzymatic digestion, the enzyme is used in great excess (10 times the amount recommended by the supplier) and the digestion time is five hours instead of one hour. Digestion is then verified on gel.

Three bands are revealed: 1600 bp, 1800 bp and 2200 bp. These results show that the plants analysed are indeed transgenic, since they contain one or two copies of the C1-Ala gene. They also suggest that the primary regenerant (Ala1) contained at least three copies of the C1 gene.

2. Detection of the C1-Ala Protein in Transgenic Plants

The C1-Ala protein in the Ala1 transgenic plants is analysed by Western blot. A preliminary experiment revealed numerous nonspecific bands even in a protein extract of non-transgenic *N. benthamiana*. Accordingly, a stage of preadsorption of the anti-C1 antibody with a total protein extract of non-transgenic *N. benthamiana* is carried out before incubation of the anti-C1 antibody with the membrane. This stage is necessary to exhaust the anti-C1 antibody solution of antibodies which recognize the antigens of *N. benthamiana* aspecifically.

The antibody directed against the C1 protein recognizes a band of about 40 kDa, the size expected for this protein. This band is present in the transgenic plants Ala1, D, S, U, and V, but is absent from non-transgenic *N. benthamiana* and the STYLCV-sensitive Ala1 B plant. Note that the Ala1 plant should be "resistant" according to the squash test but "sensitive" according to the results of agroinoculation of leaf discs. This "ambiguous" behaviour might correspond to the production of this 40 kDa band.

These results demonstrate that the C1-Ala protein is expressed in the Ala1 transgenic plants. They show a correlation between expression of the mutated C1-Ala protein and resistance to STYLCV.

Conclusion a) The P-loop of the C1 Protein is Essential for Replication

Protoplasts offer a quick and powerful means for investigating the replication of viral DNA, independently of the processes of systemic movement of the virus. Following transfection of protoplasts by the wild-type viral genome, the various forms of single-stranded (ss) and supercoiled double-stranded (ds) viral DNA accumulate and are detected. The ds form corresponds to a de novo synthesis, rather than to a ligation of the linear viral DNA introduced. This has been shown for the WDV (Matzeit et al. 1991). The authors used a restriction enzyme (DpnI) which recognizes and cuts only the sequence GA$^m$TC, the adenine of which is methylated at position N6. The viral DNA amplified in *E. coli* is digested by DpnI, whereas the ds form of transfected wheat cells is resistant to digestion. This shows that the ds form is newly synthesized in the transfected cells. However, a demethylation of the DNA introduced into the transfected cells cannot be excluded. Use of plasmid containing a dimer in tandem (instead of a linearized DNA) leads to formation of the same forms (ss and ds) which therefore correspond to a de novo synthesis.

ATPase activity in vitro has been demonstrated for the C1 protein of the wild-type STYLCV (Desbiez, DEA 1993). This activity is absent in the mutated proteins C1-Ala and C1-His, and reduced in the mutated protein C1-Arg. Here, we show a clear correlation between ATPase activity and replication of these mutants in tomato protoplasts. These results show that the NTP-binding site (P-loop) is involved, directly or indirectly, in replication of the viral DNA. On the other hand the mutant pTYArg (which carries a substitution of the lysine 227 by arginine) replicates but not so well as the wild-type. Replacement of the lysine residue 227 by arginine, an amino acid that is similar in its structure and its charge (positive at physiologic pH) to the lysine residue, seems to have a slight effect on the activity of the C1 protein. This is not the case for the alanine and histidine residues. These results suggest an essential role of lysine 227 of the P-loop in the replication of viral DNA.

Numerous examples, in other animal and viral systems, have emphasized the importance of this P-loop and especially of the conserved lysine residue. The RAD3 protein of *Saccharomyces cerevisiae* is involved in the repair of DNA lesions. Substitution of lysine 48 of the P-loop by an arginine residue leads to a loss of ATPase and DNA helicase activities of this protein (Sung et al., 1988). The Rep protein of AAV is involved in the replication of viral DNA. Substitution of lysine 340 by a histidine produces a mutant virus that is incapable of replicating (Chejanovsky et al., 1990).

b) The C1 Protein of TYLCV: What are its Roles in the Replication of Viral DNA?

Protein C1 (or its homologue AL1 in geminiviruses with a bipartite genome) is essential for the replication of viral DNA. Among the various geminiviruses, the AL1 protein of TGMV has been studied most. However, the roles of this protein in replication have not been elucidated thoroughly. It has been shown that the AL1 protein of TGMV recognizes specifically a sequence of about 50 nt at the level of the common region, and recognizes single-stranded DNA preferentially (Lazarowitz et al., 1992b; Thömmes et al., 1993). This specific interaction is necessary for the initiation of replication. For the C1 protein of TYLCV it has been shown that it possesses a site-specific endonuclease activity at the level of the highly-conserved nonanucleotide in the potential rod-loop structure of all the known geminiviruses. The AL1 protein of TGMV also possesses negative self-regulation activity on its own transcription (Sunter et al., 1993). The protein domain responsible for the repression activity has been identified for the AL1 protein of TGMV. The significance of this feedback control is still unknown. The hypothesis that we are putting forward is that the C1 protein would be sufficient for the viral cycle in a very small quantity, hence the feedback control phenomenon observed. It might be that overexpression of C1 protein is detrimental to the host cell and consequently to the virus itself which merely utilizes the cellular machinery.

The presence, in protein C1 (and AL1), of a conserved motif GxxxxGKT/S, corresponding to the NTP-binding site (P-loop), led to a potential role of DNA helicase being attributed to this protein (Gorbalenya and Koonin, 1993). This DNA helicase activity might, for example, facilitate fixation of the cellular complex of DNA polymerase as is the case for the T antigen of SV40 (Dodson et al., 1987). Demonstration of ATPase activity in vitro for the C1 protein of TYLCV has reinforced this hypothesis. However, all the known DNA helicases, with the exception of that of the cowpox virus (Traktman et al., 1993), possess a DNA-dependent ATPase activity. Tests in vitro of ATPase activity of the C1 protein of TYLCV showed that it was DNA (single-stranded and double-stranded)-independent. It is possible that the conditions used are not optimum for demonstrating this dependence. On the other hand, the C1 protein used is in the form of GST-C1 fusion expressed in a prokaryote *E. coli*. Consequently, post-translation changes (phosphorylation, glycosylation, myristylation etc.) and/or oligomerizations might be necessary for expression of this potential DNA helicase activity (or topoisomerase or other (s) unknown), and these changes do not occur in *E. coli*. Finally, it is also possible that fusion with GST affects the normal functioning of the C1 protein. It is interesting to note that at least two potentially phosphorylatable sites exist at the level of the P-loop: RXX<u>T</u> (consensus site of calmodulin-dependent protein kinases and R<u>T</u>KG consensus site recognized by the type-C protein kinases (Hofer et al., 1992).

The ATPase activity determined in vitro possesses a specific activity (s.a.) of the order of $3\times10^{-2}$ mol of ATP hydrolysed/min/mol of protein, which is very low compared with the ATPases adenylate kinases for example, which have an s.a. of the order of $2\times10^{6}$ (Hampton and Slotin, 1975). If an ATPase activity does exist in vivo and with s.a. value comparable to that determined in vitro, undoubtedly it would not serve to supply the energy necessary for a function, for example helicase or topoisomerase, but would probably permit a change of conformation of the C1 protein itself, inducing either the formation of a multimer of C1, or interaction with factors of the host. The Hsp70 protein of *E. coli* possesses an activity of the "chaperon" type, i.e. it is capable of binding to other proteins (Buchberger et al., 1994). This function is linked to an ATPase activity with s.a. of the order of $3.5\times10^{-2}$. Fixation, and probably hydrolysis of the ATP would induce a change of conformation of the Hsp70 protein necessary for its "chaperon" activity. It is possible that a change of conformation also occurs with the C1 protein and that it is necessary for its activity.

c) Dominant Negative Effect on Replication of Wild-type Viral DNA

When tomato protoplasts are cotransfected with pTY and pTYArg, the replication of the viral DNA is not altered: the DNA of pTY replicates and that of pTYArg also replicates alone, at a level less than the wild-type genome. The same result is observed with pTY and pTYHis, although the latter does not replicate alone in tomato protoplasts. The C1-His protein therefore does not have a detectable dominant effect on the replication of the wild-type. It is possible that substitution of the lysine residue by the amino acid histidine has an effect on oligomerization or its potential interaction with other factors (see below). On the other hand, it might be thought that the wild-type C1 protein would "complement" the deficiency in replication of the mutant pTYHis. To show this, it would be necessary to cotransfect tomato protoplasts with on the one hand pTYHis, and on the other hand a plasmid construct containing the wild-type C1 ORF under control of a strong promoter (35S of CaMV for example). If our hypothesis is correct, we ought to observe replication of the pTYHis mutated viral DNA.

Cotransfection of tomato protoplasts with pTY and pTYAla, the genome of which does not replicate alone, causes a marked decrease of replication of the wild-type. This result corresponds to a dominant negative effect in trans of the mutant pTYAla on replication of the wild-type, and accompanies similar preliminary results obtained with tobacco protoplasts (Mettouchi, DEA 1992). Recently, an example of dominant negative mutation was obtained for an RNA virus, Potato Virus X (PVX) (Longstaff et al., 1993). The protein of 188 K of the PVX contains a conserved GDD motif among the RNA polymerases. Expression of this protein that is modified at the level of the GDD motif in transgenic plants of N. tabacum (cv. Samsun NN) leads to resistance to PVX (absence of accumulation of viral RNA).

Two models can account for the dominant negative effect observed (Herskowitz, 1987). Either the mutated protein C1-Ala competes with the corresponding wild-type protein for a substrate or a factor (activator? repressor?) that is present in limited quantity, or it combines with the corresponding wild-type protein (or a host factor) to form a non-functional heteromultimer (i.e. one that is inactive or very quickly degradable).

The dominant negative effect of the mutated protein on the wild-type protein was investigated in vitro for ATPase activity. The result obtained did not show any negative effect with respect to utilization of ATP. However, no conclusion can be made regarding an effect in vivo, as the C1 protein is in the form of GST-C1 fusion expressed in E. coli. If this model of titration of a limiting factor (for example an activator or a repressor) by the mutated protein actually occurs in vivo, it would suffice to overexpress the wild-type protein under a strong promoter to counterbalance the dominant negative effect (provided, of course, that the mutated protein does not have a very great affinity for the limiting factor).

The second model proposes the formation of a non-functional heteromultimer between the wild-type and mutated protein (and/or another factor of the host). It might be thought that the heteromultimer no longer recognizes the specific sequence of the intergenic region, that it would have lost the capacity for negative self-regulation, that it would be unstable or very quickly degradable. To verify this second model, it would first be necessary to demonstrate, in a eukaryotic system, the existence of such oligomers or heteromultimers of protein C1.

In the absence of biochemical functions that are clearly attributed to the C1 protein, it is difficult to choose between the two models. Identification of factor(s) of the host interacting with the C1 protein as well as determination of the tertiary and quaternary structures of the latter would make it easier to choose the appropriate model to account for the dominant negative effect observed and hence elucidate the roles of the C1 protein in the replication of viral DNA.

d) Transgenic Plants Expressing C1-Ala are Resistant to TYLCV

Two types of results were obtained during analysis of the TYLCV resistance of the F1 filial generation of plants transformed with the various mutated C1 genes. The F1 plants His21, Arg1 and Stop6 are all sensitive to STYLCV. The F1 Ala1 filial generation shows, for five plants out of 14 analysed, resistance to this virus. The results reinforce those obtained with cotransfection experiments, in which only the mutant pTYAla inhibits replication of the wild-type genome.

We used three experimental techniques to test the resistance of these plants to TYLCV. The first level is based on detection of the single-stranded (ss) virus form by the leaf squash technique. The second level consists of extracting the plant's total DNA and analysing the various forms of viral DNA by Southern blot. Finally, the third level employs the method of agroinoculation of leaf discs from these plants with STYLCV. This last method is much used in programmes for selection for resistance to TYLCV (and to geminiviruses in general).

Using these three approaches, we were able to obtain two types of response. Three Ala1 plants exhibit incomplete resistance to STYLCV, since the agroinoculation of leaf discs from these plants leads to a low level of replication relative to the sensitive plants. The Ala1 plants exhibit complete resistance (no replication is observed with the three experiments).

Curiously, two Ala1 plants which, on the basis of the results of the squash test and Southern blot, would be resistant, behave as sensitive plants (with an elevated level of replication) after agroinoculation of leaf discs. We interpreted this phenotype as corresponding either to an increased "inoculum pressure" altering the ratio of mutated C1 protein to wild-type C1 protein, or probably to inhibition of viral movement in planta.

Note that the aforementioned seven Ala1 plants do not display any symptom characteristic of TYLCV even three months after their agroinoculation.

These results suggest a dominant negative effect in planta and in trans of the overexpressed mutated C1-Ala protein on the replication of the wild-type viral DNA. The mechanism accounting for this effect in planta is probably the same as that occurring in the protoplasts.

We have analysed the presence and expression of the C1-Ala gene introduced in these resistant plants. The gene is actually present in one or two copies in the resistant plants but also in some sensitive plants that were analysed. No correlation can be established between on the one hand the presence and number of copies of the C1-Ala gene and on the other hand the resistance. This may be due either to a position effect (insertion in a "silent" region of the genome), or to a modification of the gene leading to sensitivity to TYLCV.

The TYLCV-resistant Ala1 plants all express the C1-Ala protein, whereas no sensitive plant, with the exception of one of them, expresses it. While waiting to analyse more Ala1 plants (and other F1 Ala plants available), we can say that there is a correlation between expression of the protein and resistance.

APPENDIX media for tomato protoplasts

| MSI medium | | | CPW medium | | |
|---|---|---|---|---|---|
| MS salts (Sigma) | 4.6 | g | mannitol | 440 | mM |
| Morel vitamins | 1 | ml | MES | 100 | mM |
| saccharose | 20 | g | $CaCl_2$ | 10 | mM |
| myoinositol | 100 | mg | $KH_2PO_4$ | 0.19 | mM |
| 2,4 D | 1 | mg | $KNO_3$ | 1 | mM |
| $CaCl_2.2H_2O$ | 7 | mM | $MgSO_4$ | 1 | mM |
| $H_2O$ (q.s.p.) | 1 | liter | $H_2O$ (q.s.p.) | 1 | liter |
| pH 5.7 | | | pH 5.7 | | | enzyme solution of tobacco protoplasts (in CPW)

| | | | |
|---|---|---|---|
| cellulase | 2% | | |
| macerozyme | 0.1% | | |
| pectolyase | 0.01% | | |
| TM2 medium | | medium F | |

-continued

APPENDIX

| | | | |
|---|---|---|---|
| macroelements | 100 ml | NaCl | 140 mM |
| microelements | 1 ml | KCl | 5 mM |
| vitamin | 1 ml | Na$_2$HPO$_4$ | 0.75 mM |
| saccharose | 68.4 g | glucose | 54 mM |
| mannitol | 4.6 g | CaCl$_2$ | 150 mM |
| xylitol | 3.8 g | MES | 1 mM |
| sorbitol | 4.6 g | pH 5.5 | | extraction buffers

Buffer TE: Tris 10 mM, EDTA 1 mM, pH 7.5–8
Buffer TNES                          Buffer X

| (DNA extraction from plants) | | (DNA extraction from tobacco and tomato protoplasts) | |
|---|---|---|---|
| Tris-HCl (pH 8) | 100 mM | Tris-HCl (pH 8) | 100 mM |
| NaCl | 100 mM | NaCl | 100 mM |
| EDTA | 10 mM | EDTA | 50 mM |
| SDS | 1% | SDS | 0.5% | culture media

| medium YEB (for agrobacteria) | | medium MS30 | |
|---|---|---|---|
| Bacto-beef extract | 5 g | MS salts (macro and trace elements (Sigma)) | 4.6 g |
| Bacto-yeast extract | 1 g | saccharose | 30 g |
| peptone | 6 g | H$_2$O (q.s.p.) | 1 liter |
| sacharose | 5 g | pH 5.8 | |
| MgSO$_4$ | 0.5 g | | |
| H$_2$O (q.s.p.) | 1 liter | (MS = Murashige and Skoog) | |
| pH 7.2 | | | |
| medium A | | medium B | |

| | | | |
|---|---|---|---|
| MS30 + ANA | 0.1 g/l | medium A+ | |
| BAP | 1 g/l | kanamycin | 70 mg/l |
| Morel vitamins | | cefotaxime | 500 mg/l | solutions for Southern analysis

| TAEx1 | | SSCx20 | |
|---|---|---|---|
| Tris-acetate | 0.04M | NaCl | 175 g |
| EDTA | 0.001M | Na citrate | 88 g |
| | | H$_2$O (s.q.f) | 1 liter |
| TBEx1 | | | |
| Tris-borate | 0.09M | | |
| EDTA | 0.002M | | | hydridization solution

| | |
|---|---|
| NaH$_2$PO$_4$ | 0.5M |
| SDS | 7% |
| EDTA | 1 mM |
| BSA | 10 g/l | solutions for Western analysis

| PBS (Phosphate-buffered saline) | | Substrate buffer (for alkaline phosphatase) | |
|---|---|---|---|
| NaCl | 140 mM | NaCl | 100 mM |
| KCl | 2.7 mM | MgCl$_2$ | 5 mM |
| Na$_2$HPO$_4$ | 10 mM | Tris-HCl (pH 9.5) | 100 mM |
| KH$_2$PO$_4$ | 1.8 mM | | |
| pH 7.3 | | | |
| Buffer 6xSDS | | | |
| Tris-HCl (pH 6.8) | 350 mM | | |
| SDS | 0.3% | | |
| glycerol | 36% | | |
| DTT | 9% | | |
| Bromophenol blue | 0.012% | | |

Media and gels used for studying the Rep protein in vitro

MTPBS medium

| | |
|---|---|
| *NaCl | 100 mM |
| *Na$_2$HPO$_4$ | 16 mM |

-continued

APPENDIX

| | |
|---|---|
| *NaH$_2$PO$_4$ | 4 mM |
| pH 7.3 | |

Composition of the Gels Used: 10% Laemmli Gel

| Settlement gel (2.5 ml) | | Resolving gel (5 ml) | |
|---|---|---|---|
| H$_2$O | 1.9 ml | H$_2$O | 1.67 ml |
| Tris 1M pH 6.8 | 0.31 ml | Tris 1M pH 8.8 | 1.63 ml |
| SDS 20% | 30 µl | SDS 20% | 30 µl |
| Acrylamide-bisacrylamide 30% | 0.32 ml | Acrylamide-bisacrylamide 30% | 1.65 ml |
| APS 10% | 25 µl | APS 10% | 25 µl |
| TEMED | 4 µl | TEMED | 4 µl |

Solution of Coomassie Blue:
  2.5 mg/l of Coomassie Brilliant Blue R250
  20% ethanol
  10% acetic acid
  The gels are left to stain in this solution over night, then the excess dye is removed by rinsing in a mixture of 20% ethanol—10% acetic acid for at least one hour.

| | | |
|---|---|---|
| Medium I: | MS30 + ANA | 0.1 mg/l |
| | BAP | 1 mg/l |
| Morel vitamins: | Ca pantothenate | 1 mg/l |
| | Meso-Inositol | 100 mg/l |
| | Biotin | 0.01 mg/l |
| | Nicotinic acid | 1 mg/l |
| | Pyridoxine (Vit. B6) | 1 mg/l |
| | Thiamine (Vit. B1) | 1 mg/l |
| Medium II: | Medium I + kanamycin | 70 mg/l |
| | cefotaxime | 500 mg/l |
| Medium III: | Medium II without ANA and BA | |

The three media are used solid (agar 9 g/l).

IV) CONSTRUCTION OF TRANSGENIC TOMATOES (L. esculentum) EXPRESSING THE MUTATED REP PROTEINS AND PROTECTED AGAINST PATHOLOGIES CAUSED BY STYLCVs 1) Protocol Used for Genetic Transformation of the Tomato (Lycopersicon esculentum)

The protocol followed is based on two publications.

On the one hand that of S. McCormick et al. (1986): Leaf disk transformation of cultivated tomato (Lycopersicon esculentum) using Agrobacterium tumefaciens. Plant Cell Reports 5:81–84, and on the other hand that of J. J. Fillati et al. (1987): Efficient transfer of a glyphosate tolerance gene into tomato using a binary Agrobacterium tumefaciens vector. Bio/technology 5:726–730.

The explants used are young cotyledons that are still growing, before emergence of the first leaves.

They are obtained from sterile germinations in vitro.

Strains of agrobacterium containing the plasmids that include the gene of interest (namely the C1* mutated nucleotide sequences as shown in FIG. 13) are cultivated in a liquid medium for two days at 28° C., in the dark and with stirring.

The sequence of operations is as follows:

Day 1: culture of the bacteria in minimum medium with antibiotics. Preparation of Petri dishes (solid medium) containing a suspension of tobacco cells in full growth: these are the nursery beds.

Day 2: careful cutting of fragments of cotyledons (two fragments per cotyledon), avoiding any oxidation of the tissues (under water). Culture of these fragments, upper surface downwards, on nursery beds previously covered with a Whatman No. 1 filter paper. This incubation must continue for at least 8 hours, at 25° C., in dimmed light.

Day 3: centrifugation of the agrobacteria and placing them in a medium suited to plant tissues, taking care to adjust the OD (at 590 nm) of the suspension between 0.4 and 0.5.

Rapid immersion of the tomato explants in this suspension and culture of them on the same nursery beds: this is plant-bacteria co-culture, and is continued for 40 hours, at 25° C., in dimmed light.

Day 5: transfer of the explants to a medium permitting regeneration of buds (growth regulators) and selection of the transformed cells (appropriate antibiotics). The fragments of cotyledons are then deposited according to normal polarity. They are transferred to new media every two to three weeks, until buds appear.

When the buds are well-developed, they are placed on a medium that permits rooting. When well rooted, the plants are acclimatized in a greenhouse.

Media used for transformation of the tomato:
Media for Bacteria:
Minimal medium for culture of agrobacteria, for 1 liter:

| | | |
|---|---|---|
| $K_2HPO_4$ | 10.5 g | |
| $K_2HPO_4$ | 4.5 g | |
| $(NH_4)_2SO_4$ | 1.0 g | |
| Sodium citrate-$2H_2O$ | 0.5 g | |

Autoclave at 120° C., 30 min, in a total volume of 990 ml. Before use, add the following sterile compounds, also sterilized by autoclave

| | | |
|---|---|---|
| $MgSO_4.H_2O$ 1M | 1 ml (120° C., 30 min) | |
| Glucose 20% | 10 ml (110° C., 30 min) | |

Sterilized by Filtration (0.45 μm).
Tetracycline to a Final Concentration of 5 mg/l for the Vector Used.

Liquid medium for resuspension of the agrobacteria:
Mineral elements of Murashige and Skoog, already described above for the transformation of *Nicotiana benthamiana*:

| | | |
|---|---|---|
| Saccharose | 30 g | |
| pH | 5.8 | |

Autoclave at 110° C. for 20 min.
Media for Plants:
Medium for germination of tomato seeds:
For 1 liter:
Mineral Elements of Murashige and Skoog

| | | |
|---|---|---|
| Saccharose | 30 g | |
| Agarose | 6 g | |
| pH | 5.8 | |

Autoclave at 110° C. for 20 min. Pour into sterile culture tubes.

Medium for the BY2 suspension:
Already described above for maintenance of this cell suspension, also used for the transfection of tobacco protoplasts.

This medium is simply solidified with 0.6% of agarose and poured into Petri dishes. One ml of suspension is spread over its surface.

Medium permitting selection of the transformed cells and the regeneration of buds:
For 1 Liter:

| | | |
|---|---|---|
| Mineral elements of Murashige and Skoog | | |
| Myo-inositol | 100 mg | |
| Saccharose | 20 g | |
| Gelrite (Serva) | 2 g | | pH 6.0
Autoclave at 110° C. for 20 min.
Before use, add the following compounds, sterilized by filtration:

| | | |
|---|---|---|
| Zeatin riboside | 2 mg | |
| Nitsch vitamins: | | |
| Thiamine | 0.5 mg | |
| Glycine | 2.0 mg | |
| Nicotinic acid | 5.0 mg | |
| Pyridoxine | 0.5 mg | |
| Folic acid | 0.5 mg | |
| Biotin | 0.05 mg | |

A solution of this mixture at 1000-fold concentration is prepared, fractionated in 1 ml volumes and stored at −20° C.
For 1 liter of medium, add 1 ml of stock solution.
Antibiotics:

| | | |
|---|---|---|
| Cefotaxime | 500 mg (to eliminate the agrobacteria) | |
| Kanamycin | 100 mg (selection of the transformed cells) | |

Rooting medium:
For 1 liter:
Mineral Elements of Murashige and Skoog at Half Dilution

| | | |
|---|---|---|
| Saccharose | 5 g | |
| Gelrite | 2 g | |
| pH 6.0 | | |

Autoclave at 110° C. for 20 min.
Before use, add the following compounds, sterilized by filtration:

| | | |
|---|---|---|
| Cefotaxime | 200 mg | |
| Kanamycin | 50 mg | |

2) Agroinoculation of Tomatoes (*Lycopersicon esculentum*) with STYLCV
Agroinoculation experiments were conducted following the method described above for *N. benthamiana*.

Plants inoculated: T0 primary regenerants perfectly rooted in vitro on the selective in vitro culture medium containing kanamycin (50 mg/l).

Results obtained after molecular hybridization according to the squash blot technique using total DNA from STYLCV, labelled with $^{32}P$, as probe.

General conclusion: of a set of 11 independent T0 primary regenerants, 4 obtained with the Ala construct and 7 with the His construct, 4 (2 with one of the constructs and 2 with the other) are without viral DNA after replication and are therefore good candidates for resistance to the virus STYLCV (see the accompanying Table 1).

TABLE 1

| Primary regenerants | Total number inoculated | Test on 21/07/95 S | Test on 21/07/95 R | Total number inoculated | Test on 11/08/95 S | Test on 11/08/95 R |
|---|---|---|---|---|---|---|
| T0 inoculated | | | | | | |
| Cultivar I$^{Ala}$ a | 9 | 4 | 5 | 25 | 16 | 9 |
| b | 1 | 1 | 0 | 2 | 2 | 0 |
| c | 1 | 1 | 0 | 3 | 1 | 2 |
| Cultivar II a | not tested | | | 1 | 1 | 0 |
| Cultivar I$^{His}$ a | 1 | 0 | 1 | 2 | 2 | 0 |
| Cultivar II a | 1 | 0 | 1 | 1 | 1 | 0 |
| b | 1 | 1 | 0 | 1 | 1 | 0 |
| c | 1 | 1 | 0 | 2 | 0 | 2 |
| Cultivar III a | 1 | 1 | 0 | 2 | 2 | 0 |
| Cultivar IV a | 2 | 1 | 1 | 5 | 3 | 2 |
| b | 1 | 1 | 0 | 1 | 1 | 0 |

S: sensitive plant, viral DNA present on squash blot
R: resistant plant, DNA absent.

The numbers are small because these are the first transgenic tomato plants obtained, gradually acclimatized in the greenhouse.

V) AGROINOCULATION OF *NICOTIANA BENTHAMIANA* WITH THE JORDANIAN ISOLATE OF ITYLCV (ITYLCV-Jo):

Agroinoculation experiments were conducted according to the protocol described above.

Plants inoculated: T2 filial generation, or second generation obtained after self-fertilization of T1 plants containing Ala and his mutations which are resistant to STYLCV, and which produce the mutated Rep protein in large quantity.

Results obtained after molecular hybridization according to the squash blot technique using total DNA from ITYLCV-Jo, labelled with $^{32}P$, as probe.

General conclusions: in a set of T2 plants derived from four T1 plants selected for the presence of Rep and resistance to STYLCV and during two repetitions of the same experiment, some of them show resistance to another virus, ITYLCV-Jo, the nucleotide sequence of which only exhibits 75% homology with that of STYLCV.

The resistance conferred by the production of an altered Rep protein coded by a mutated C1 sequence of STYLCV therefore seems to induce resistance to another geminivirus, ITYLCV-Jo (see the accompanying Table 2). Moreover, these viruses are sufficiently distant so that there cannot be cross complementation for the functions of the Rep protein (Jupin I., Héricourt F., Benz B. and Gronenborn B. (1995), DNA replication specificity of TYLCV geminivirus is mediated by the aminoterminal 116 amino acids of the Rep protein, FEBS Letters, 362: 116–120.

TABLE 2

| T1 plants | Number of T2 inoculated | Test on 23/06/95 S | Test on 23/06/95 R | Number of T2 inoculated | Test on 03/08/95 S | Test on 03/08/95 R |
|---|---|---|---|---|---|---|
| His a | 11(10) | 1(6) | 10(4) | 12 | 11 | 1 |
| b | 10(12) | 5(10) | 5(2) | 23 | 21 | 2 |
| Ala a | 11(8) | 6(4) | 5(4) | 22 | 18 | 4 |
| b | 10(9) | 7(2) | 4(7) | 23 | 23 | 0 |

S: sensitive plant, viral DNA present on squash blot
R: resistant plant, DNA absent.
(x): results obtained in parallel after inoculation of the STYLCV Figure Captions:

FIG. 1: Genomic organization of STYLCV. The black arrows represent the ORFs of the viral strands (V1 and V2) and complementary (C1, C2, C3, C4) strands. The position of the hairpin structure is indicated by (i). ORF V1 seems to code for a protein involved in systemic movement, ORF V2 codes for the capsid protein, ORF C1 codes for the only protein indispensable for replication, ORF C2 codes for an activator of transcription of the ORFs of the viral strand, and ORFs C3 and C4 have no known functions;

FIG. 2: Diagrammatic representation of the plasmids pTY Ala, His, Arg, plasmid pBMC-S and plasmids pC1 Ala, His, Arg, the principal restriction sites of these various plasmids are indicated;

FIG. 3: the mutations affect the codon of lysine at position 227 (encoded by AAG) and result in its substitution by Ala (encoded by GCG), His (encoded by CAT) and Arg (encoded by AGG);

FIG. 4: replication of the mutants at the NTP-binding site of STYLCV; the autoradiogram resulting from Southern analysis is quantified by means of an image analyser (Bio-Images, Millipore), which assigns an optical density value to the spots. The graph shows the percentage of replicative forms after three (in black) and five (in white) days of culture of the transfected cells. pTYLCV: wild-type viral genome; pTYAla, pTYArg: mutated viral genomes corresponding to change of K to A and R respectively;

FIG. 5: graph resulting from quantification of the autoradiogram obtained during investigation of a trans-dominant effect of mutation K to R, by an NPT II activity test. The constructs indicated in the document were cotransfected with the recombinant viral genome coding for neomycin phosphotransferase (pTYNeo). NPT II activity is investigated after 3 and 5 days of culture of the transfected cells. The intensities were normalized relative to the signal corresponding to cotransfection of the recombinant genome with the pUC vector.

Figure 6:
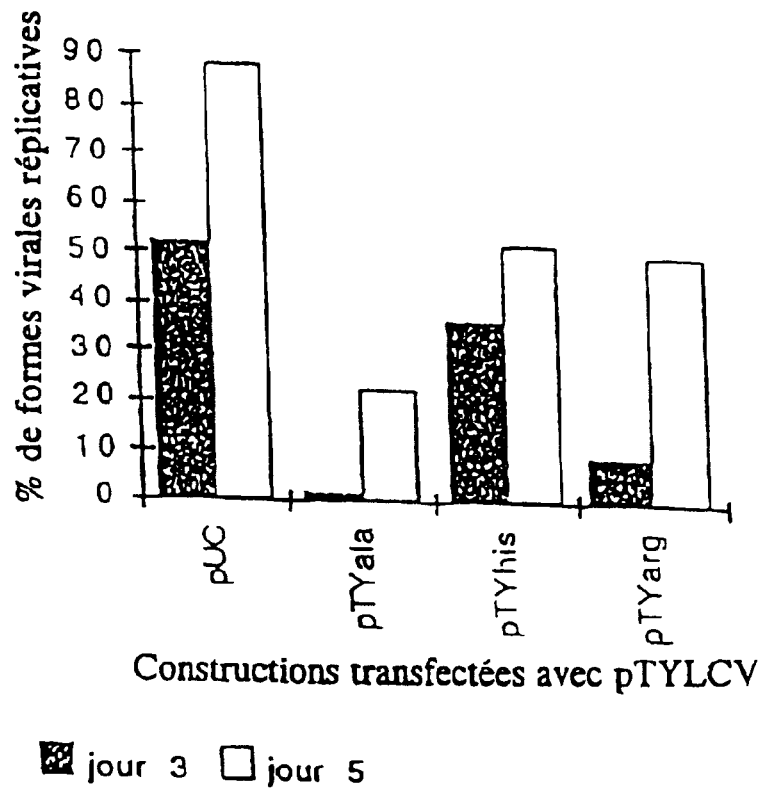
FIG. 6: graph representing the effect of transfection of mutant viral genomes (pTYAla, pTYHis, pTYARg) on replication of the wild-type virus (pTYLCV)
Figure 8:
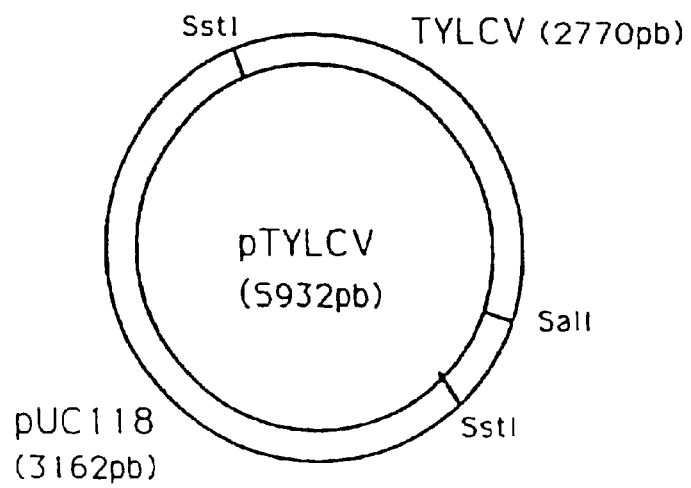
FIG. 8: representation of the plasmids pTYLCV and pGEXC1.
Figure 8:
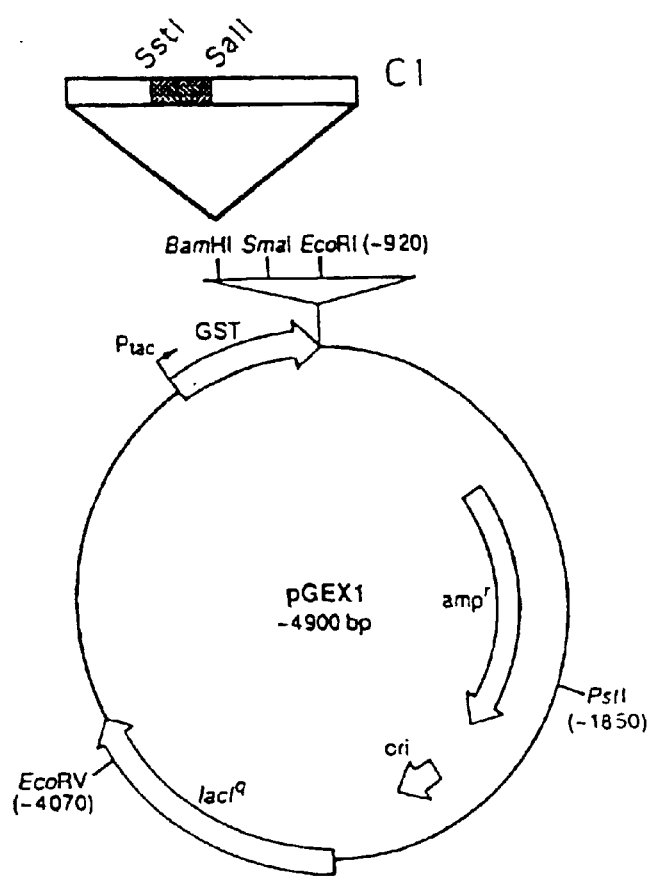
Figure 9:
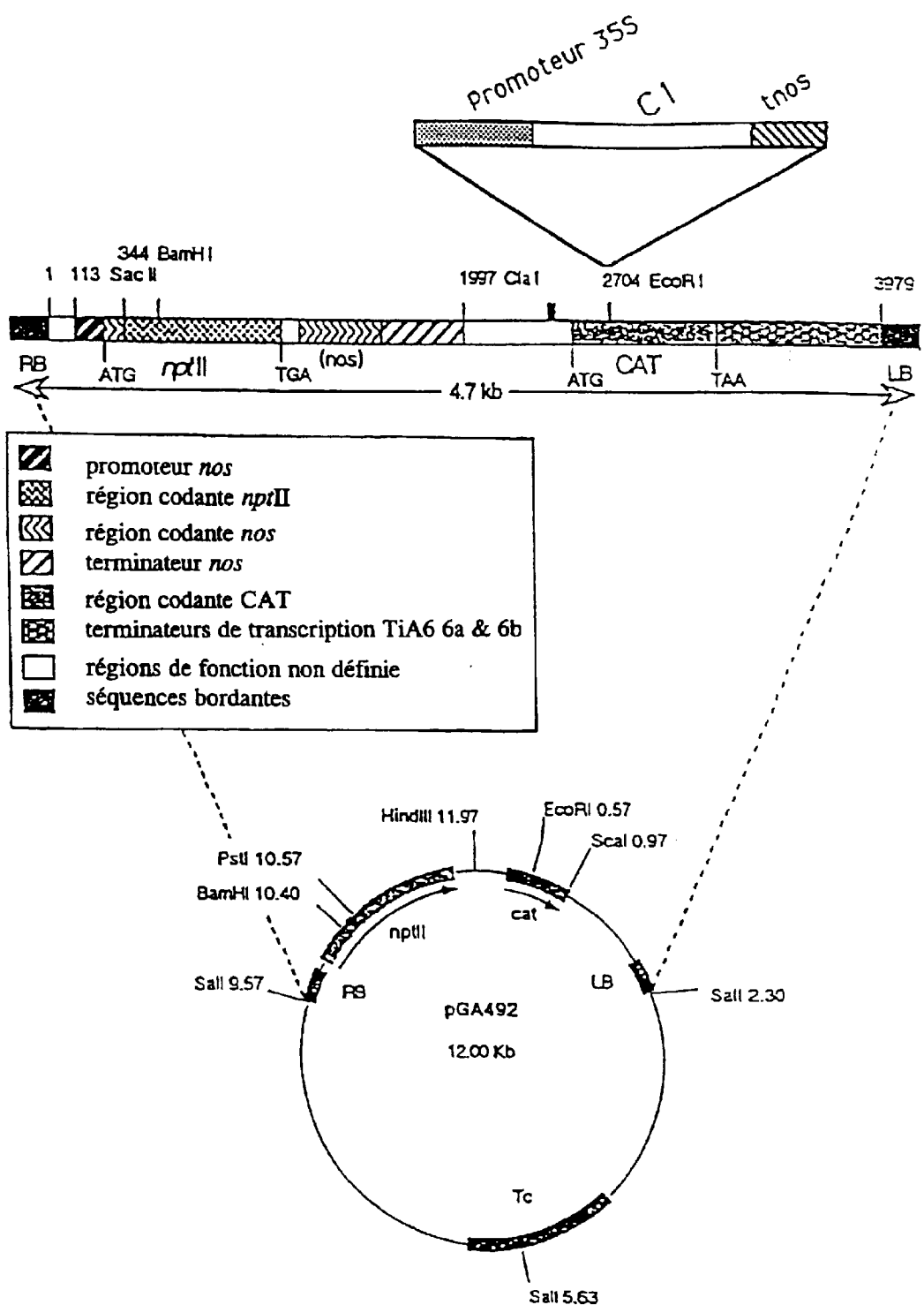
FIG. 9: cloning of the ORF C1 downstream of the promoter 35S in plasmid pGA492.

FIG. 6: graph resulting from quantification of the autoradiogram obtained during investigation of the effect of transfection of mutated viral genomes (pTYAla, pTYHis, pTYArg) on replication of the viral genome (pTYLCV). The percentage of replicative forms is shown for the various samples after 3 and 5 days of culture of the transfected cells. The control corresponds to cotransfection of the wild-type virus with the pUC vector so as to transfect the same quantity of DNA;

FIG. 7: graph resulting from quantification of the autoradiogram obtained during investigation of the effect of cotransfection of constructs permitting the high-level expression of mutated C1 proteins (pC1Ala, pC1His, pC1Arg) on replication of the viral genome (here pTYNeo);

FIG. 8: the plasmids pTYLCV and pTY-Ala, Arg, His, Pml and Stop are composed of the plasmid pUC118 in which the entire genome of the wild-type or mutated TYLCV is cloned at the single site SstI. The plasmid pGEXC1 consists of the plasmid pGEX3 (Amrad) in which the C1 gene is cloned at site BamHI. The lac repressor, produced from the lacI gene, binds to the promoter Ptac and represses expression of the fusion protein GST-C1. In the presence of IPTG, expression of the fusion protein is derepressed;

FIG. 9: cloning of ORF C1 downstream from the promoter 35S in the pGA492 plasmid. This binary plasmid possesses the elements (edges of the T-DNA of *A. tumefaciens*) necessary in cis for transfer of DNA to the plants. The other elements are supplied by an auxiliary plasmid that is present in the *A. tumefaciens* strain LBA4404. The plasmids containing the mutations introduced were obtained by replacing a fragment SstI-BglII (SstI-PflmI for the Stop mutant) of the wild-type C1 gene by a mutated gene. The construct is then cloned at the single site EcoRI of the pGA492 plasmid;

FIG. 10: transformation of leaf discs of *N. benthamiana* and production of transgenic plants expressing the wild-type or mutated C1 ORF. Starting from a young plant of *N. benthamiana* about three weeks old, young leaves are taken and sterilized. Leaf discs are cut out with a punch, then immersed for 30 seconds in a culture of *A. tumefaciens* containing the construct to be introduced. Then the discs are cultured for 2 days on budding medium (medium I) without antibiotics. They are transferred onto medium II (with kanamycin+cefotaxime) every ten days until buds appear. The plantlets obtained are transplanted onto rooting medium III (without hormones), then in a greenhouse on vermiculite with watering with the nutrient solution. The composition of the media I, II and III is given in the appendix.

FIG. 11: simplified explanatory diagram for obtaining plants of the first generation F1;

FIG. 12: replication of viral DNA in tomato protoplasts. The protoplasts are either transfected (wells 1 to 4 and 8), or cotransfected (wells 5 to 7 and 9) with the wild-type or mutated viral genome. Seven days later, the total DNA is extracted, separated in an agarose gel and transferred onto nylon membrane. Hybridization is effected with a probe corresponding to the total DNA of TYLCV-Sar labelled with $^{32}P$. Exposure for 15 h at −70° C. ss: single-stranded form; ds: supercoiled double-stranded form; lin: linear form.

FIG. 13: sequences of nucleic acids and amino acids of the mutated C1 ORFs (C1*) of STYLCV and of the corresponding altered Rep proteins. The nucleotide sequence begins at the initiator ATG. The Rep protein comprises 359 amino acids. The wild-type nucleic acids (SEQ ID NO:1) and amino acids (SEQ ID NO:2) are indicated with capitals. The mutated nucleic acids are indicated with lower-case letters and the mutated amino acids are indicated by italicized capitals. Codon No. 227 (AAG) coding for lysine (K) of the wild-type Rep protein was replaced by the codon gcG (SEQ ID NO:3) to obtain the protein Rep K227A (SEQ ID NO:4), where alanine replaces the lysine. This same codon was replaced by the codon cAt (SEQ ID NO:5) to obtain the protein Rep K227H (SEQ ID NO:6), in which histidine replaces lysine. Finally, replacement of this codon by the codon AgG (SEQ ID NO:7) gives protein Rep K227R (SEQ ID NO:8), where arginine replaces lysine. (PmlI) indicates the restriction site cACGTG introduced for selection of the mutants. This is a silent mutation which does not alter the protein sequence.

BIBLIOGRAPHY

Accotto G. P., Donson J., and Mullineaux P. M. 1989. Mapping of Digitaria streak virus transcripts reveals different RNA species from the same transcription unit [published erratum appears in EMBO J 1989 November;8(11):3542]. *Embo J*, 8: 1033–9.

Allex D., Laterrot H., Kheyr-Pour A., Machoux G., et Hostachy B. 1994. La maladie des feuilles jaunes en cuillère de la tomate: une virose à venir? *PHM Revue Horticole* N 350: 13–17.

An G., 1987. Binary Ti vectors for plant transformation and promoter analysis. *Methods in Enzymology* 153: 292–305.

Ausubel F. M., Brent, R., Kingston R. E., Moore D. D., Seidman J. G., Smith J. A., Struhl K., 1989. *Current Protocols in Molecular Biology*. Wiley Interscience, N.Y.

Buchberger A., Valencia A., McMacken R., Sander C. and Bukau B. 1994. The chaperone function of DnaK requires the coupling of ATPase activity with substrate binding through residue E171. *Embo J.*, 13: 1687–1695.

Chejanovsky N. and Carter B. J. 1990. Mutation of consensus purine binding site in the adeno-associated virus rep gene generates a dominant negative phenotype for DNA replication. *J Virol.*, 64: 1764–70.

Czosnek H., Navot N., and Laterrot H. 1990. Geographical distribution of Tomato Yellow Leaf Curl Virus. A first survey using a specific DNA probe. *Phytopath. Medit.*, 29: 1–6.

Davies J. W. and Stanley J. 1989. Geminivirus genes and vectors. *Trends Genet.*, 5: 77–81.

Day A. G., Bejarano E. R., Buck K. W., Burrell M. and Lichtenstein C. P. 1991. Expression of an antisense viral gene in transgenic tobacco confers resistance to the DNA virus tomato golden mosaic virus. *Proc. Natl. Acad Sci. USA*, 88: 6721–6725.

Desbiez C. 1993. Mise en évidence d'une activité ATPase chez la protéine Rep d'un géminivirus. Etude de mutations dans son site de liaison aux NTP. Rapport de DEA de Phytopathologie. Université Paris VI, Université Paris XI et Institut National Agronomique Paris-Grignon.

Dodson M., Dean F. B., Bullock P., Harrison E. and Hurwitz J. 1987. Unwinding of duplex DNA from the SV40 origin of replication by T antigen. *Science*, 238: 964–967.

Elmer J. S., Brand L., Sunter G., Gardiner W. E, Bisaro D. M. and Rogers S. G. 1988. Genetic analysis of tomato golden mosaic virus II. Requirement for the product of the highly conserved AL1 coding sequence for replication. *Nucleic Acids Res.*, 16 7043–7060.

Eshed Y., Abu-Abied M., Saranga Y. and Zamir D. 1992. *Lycopersicon esculentum* lines containing small overlapping introgressions from *L. pennellii*. *Theor. Appl. Genet.*, 83: 1027–1034.

Fontes E P B., Luckow V A. and Hanley-Bowdoin L. 1992. A geminivirus replication protein is a sequence-specific DNA binding protein. *The Plant Cell* 4: 597–608.

Francki R. I. B., Hatta T., Boccardo G. and Randles J. W., 1980. The composition of chlorosis striate virus, a geminivirus. *Virology*, 101: 233.

Frischmuth T. and Stanley J. 1993. Strategies for the control of geminiviruses diseases. *Seminars in Virology*. 4:329–337.

Gorbalenya A. E., and Koonin E. V. 1989. Viral proteins containing the purine NTP-binding sequence pattern. *Nucleic Acids Res.*, 17: 8413–8440.

Gorbalenya A. E. and Koonin E. V. 1993. Helicases: amino acid sequence comparisons and structure-function relationships. *Current Opinion in Structural Biology*, 3: 419–429.

Grimsley N., Hohn B., Hohn T., and Walden R. 1986. "Agroinfection" an alternative route of viral infection of plants by using the Ti plasmid. *Proc Natl Acad Sci USA*, 83: 3282–3286.

Hampton A. and Slotin L. A. 1975. Inactivation of rabbit, pig and carp adenylate kinases by N6-o- and p-Fluorobenzoyl-adenosine 5'-triphosphates. *Biochemistry*, 14: 5438–44.

Han M., Sternberg P. W., 1991. Analysis of dominant negative mutations of the *Caenorhabditis elegans* let-60 ras gene. *Genes & Development* 5: 2188–2198.

Hanley-Bowdoin L., Elmer J. S., and Rogers S. G. 1988. Transient expression of heterologous RNAs using tomato golden mosaic virus. *Nucleic Acids Res* 16: 10511–18.

Harrison B. D. 1985. Advances in geminivirus research. *Annu. Rev. Phytopathol*, 23: 30–139.

Herskowitz I. 1987. Functional inactivation of genes by dominant negative mutations. *Nature*, 329: 219–222.

Hofer J. M. I., Dekker E. L., Reynolds H. V., Woolston C. P., Cox B. S and Mullineaux P. M. 1992. Coordinate regulation of replication and virion sense gene expression in wheat dwarf virus. *The Plant Cell*, 4: 213–223.

Hostachy B., Allex D. 1993. Un nouveau défi pour les maraîchers des Antilles francaises: un géminivirus de la tomate transmis par *Bemisia tabaci*, *Phytoma* 456: 24–28.

Kato K., Matsumoto T., Koiwai A., Mizusaki S., Nishida K., Noguchi M. and Tamaki E., 1972. Liquid Suspension Culture of Tobacco Cells. *Ferment. Technol. Today*, 689–695.

Kheyr-Pour A., Bendahmane M., Matzeit V., Accotto G. P., Crespi S. and Gronenborn B. 1991. Tomato yellow leaf curl virus from Sardinia is a whitefly-transmitted monopartite geminivirus. *Nucleic Acids Res*, 19: 6763–9.

Kunkel T. A. 1985. Rapid and efficient site-specific mutagenesis without phenotypic selection. *Proc. Natl. Acad. Sci.*, 82: 488–492.

Lazarowitz S. G. 1992a. Geminiviruses: genome structure and gene function. *Critical Reviews in Plant Sciences*, 11: 327–349.

Lazarowitz S. G., Leeju C. W., Rogers S. G. and Elmer S. 1992b. Sequence-specific interaction with the viral AL1 protein identifies a geminivirus DNA replication origin. *The Plant Cell*, 4: 799–809.

Longstaff M., Brignetti G., Boccard F., Chapman S. and Baulcombe D. 1993. Extreme resistance to potato virus infection in plants expressing a modified component of putative viral replicase. *Embo J.*, 12: 379–386.

Matzeit V., Schaefer S., Kammann M., Schalk H., Schell J. and Gronenborn B. 1991. Wheat dwarf virus vectors replicate and express foreign genes in cells of monocotyledonous plants. *The Plant Cell*, 3: 247–258.

Mettouchi A. 1992. Mutants négatifs dominants dans le site de liaison de NTP de la protéine C1 du virus de la courbure et du jaunissement des feujilles de la tomate. Rapport de DEA de Microbiologie. PASTEUR.

Nagata T., Nemoto Y. and Haseawa S., 1992. Tobacco BY-2 Cell Line as the "Hela" Cell in the Cell Biology of Higher Plants. *International Revue of Cytology*: 132.

Nagy J. I. and Maliga P., 1976. Callus induction and plant regeneration from mesophyl protoplasts of *Nicotina Slylvestris Z*. *Pflanzenphysiol*, 78: 453–455.

Navot N., Ber R. and Czosnek H. 1989. Rapid detection of tomato yellow leaf curl virus in squashes of plants and insect vectors. *Phytopathology*, 79: 562–568.

Navot N., Pichersky E., Zeidan M., Zamir D. and Czosnek H. 1991. Tomato yellow leaf curl virus: a whitefly-transmitted geminivirus with a single genomic component. *Virology*, 185: 151–161.

Reiss B., Sprengel R., Will H., Schaller H., 1984. A new sensitive method for qualitative and quantitative assay of neomycin phosphotransferase in crude cell extracts. *Gene*, 30: 211–218.

Rochester D. E., Kositratana W., and Beachy R. N. 1990. Systemic movement and symptom production following agroinoculation with a single DNA of tomato yellow leaf curl geminivirus (Thailand). *Virology*, 178: 520–6.

Sambrook, Frisch and Maniatis. Molecular cloning: A laboratory manual. Cold Spring Harbor; Cold Spring Harbor Laboratory Press, 1989.

Sanger F., Nicklen S. L. and Coulson A. R., 1977. DNA sequencing with chain-terminating inhibitors. *Proc. Natl. Acad. Sci.*, 74: 5463–5467.

Sanger F., 1981. Determination of Nucleotide Sequences in DNA. *Science*, 214: 1205–1210.

Saunders K., Lucy A. and Stanley J. 1991. DNA forms of the geminivirus African cassava mosaic virus consistent with a rolling circle mechanism of replication. *Nucleic Acids Res.*, 19: 2325–2330.

Stenger D. C., Revington G. N, Stevenson M. C. and Bisaro, D. M. 1991. Replication release of geminivirus genomes from tandemly repeated copies: evidence for rolling-circle replication of a plant viral DNA. *Proc. Natl. Acad. Sci. USA*, 88: 8029–33.

Sung P., Hoggins D., Prakash L. and Prakash S. 1988. Mutation of Lysine-48 in the yeast RAD3 protein abolishes its ATPase and DNA helicase activities but not the ability to bind ATP. *Embo J.*, 7: 3263–3269.

Sung P., Hoggins D., Prakash L., Prakash S. 1988. Mutation of Lys. 68 to Arg. in yeast RAD3 protein abolishes its ATPase and DNA helicase activities but not the ability to bind ATP. *EMBO J.*, 7: 3263–3269.

Sunter G., Hartitz M. D. and Bisaro D. M. 1993. Tomato golden mosaic virus leftward gene expression: autoregulation of geminivirus replication protein. *Virology*, 195: 275–80.

Thömmes P., Osman T. A. M., Hayes R. J. and Buck K. W. 1993. TGMV replication protein AL1 preferentially binds to single-stranded DNA from the common region. *FEBS*, 319: 95–99.

Townsend R., Watts J., Stanley J. 1986. Synthetis of viral DNA forms in *Nicotina plumbaginifolia* protoplasts inoculated with cassava latent virus (CLV); evidence for independent replication of one component of the CLV genome. *Nucleic Acids Res.*, 14: 1253–1266.

Traktman P., McDonald W., Klemperer N. and Ghosh R. 1993. Molecular genetics and biochemical analysis of vaccinia virus DNA replication. in Abstract of the IXth International Congress of Virology of Glasgow (Scotland), 8–13 August.

Von Arnim A. and Stanley J. 1992. Inhibition of African cassava mosaic virus systemic infection by a movement protein from the related geminivirus tomato golden mosaic virus. *Virology*, 187: 555–64.

Walker J. E., Saraste M., Runswick M. J., Gay N. J. 1982. Distantly related sequences in the alaph- and beta-subunits of ATP synthase, kinases and other ATP-requiring enzymes and a common nucleotide-binding site. *EMBO J.*, 1: 945–95.

Zakay Y., Navot N., Zeidan M., Rabinowitch H., Czosnek H. and Zamir D. 1990. Screening of Lycopersicon accessions for resistance to tomato yellow leaf curl virus: presence of viral DNA and symptom development. *Plant Dis.*, 75: 279–281.

What is claimed is:

1. A method for producing a transgenic plant with increased resistance or tolerance to a geminivirus comprising the steps of:

deriving a mutated nucleotide sequence coding for an inactive protein C1 corresponding to the active protein C1 of a geminivirus, wherein the lysine located between positions 220 and 235 of said active protein C1 is replaced by alanine, arginine or histidine;

introducing said mutated nucleotide sequence into a plant cell to produce a transformed plant cell; and regenerating a transgenic plant from the transformed plant cell, wherein said mutated nucleotide sequence induces a dominant negative phenotype of inhibited replication, movement or plant-to-plant distribution of a geminivirus, and wherein the transgenic plant has increased resistance or tolerance to a geminivirus compared to an untransformed plant.

2. The method of claim 1, wherein the active protein C1 is SEQ ID NO:2.

3. The method of claim 1, wherein said lysine is replaced by alanine.

4. The method of claim 1, wherein the inactive C1 protein comprises alanine at position 227.

* * * * *